(12) United States Patent
Watson et al.

(10) Patent No.: US 8,557,735 B2
(45) Date of Patent: Oct. 15, 2013

(54) METHODS OF REDUCING WEEDS AND KITS THEREFOR

(75) Inventors: Alan K. Watson, N.D.I. Perrot (CA); Mohammed H. Abu-Dieyeh, Pierrefonds (CA)

(73) Assignee: The Royal Institution for the Advancement of Learning/McGill University, Montreal (CA)

( * ) Notice: Subject to any disclaimer, the term of this patent is extended or adjusted under 35 U.S.C. 154(b) by 430 days.

(21) Appl. No.: 12/740,459

(22) PCT Filed: Oct. 30, 2008

(86) PCT No.: PCT/CA2008/001918
§ 371 (c)(1),
(2), (4) Date: Aug. 17, 2010

(87) PCT Pub. No.: WO2009/055924
PCT Pub. Date: May 7, 2009

(65) Prior Publication Data
US 2011/0021354 A1    Jan. 27, 2011

Related U.S. Application Data

(60) Provisional application No. 60/983,968, filed on Oct. 31, 2007.

(51) Int. Cl.
*A01N 63/00*    (2006.01)

(52) U.S. Cl.
USPC ........................................................ 504/117

(58) Field of Classification Search
None
See application file for complete search history.

(56) References Cited

U.S. PATENT DOCUMENTS 4,782,626 A * 11/1988 Shanley et al. ..................... 47/9
5,994,267 A * 11/1999 Watson et al. ................ 504/117

OTHER PUBLICATIONS http://pr-rp.pmra-arla.gc.ca/PR SOL/pr web.vel?p ukid=11869 Apr. 20, 2007.*
Chittick A.T. et al., "Microencapsulation: an answer to the formulation quandary?" in VI International Bioherbicide Workshop Proceedings, Canberra, Apr. 27, 2003.*
Connick W.J. Jr. et al., Biological Control, vol. 1, pp. 281-287, Dec. 1991.*
Greaves M.P et al, "Formulation of microbial herbicides", in HI) Burges (ed), Formulation of Microbial Biopesticides, beneficial organisms and nematodes, Kluwer Academic Press, Dordrecht, pp. 203-233, 1998.*
Chittick A.T.I et al., "Microencapsulation: an answer to the formulation quandary?" in VI International Bioherbicide Workshop Proceedings, Canberra, Apr. 27, 2003.
Connick W.J. Jr. et al., "Formulation of Mycoherbicides Using a Pasta-like Process" Biological Control, (1991), 1, pp. 281-287.
Greaves M.P. et al., "Formulation of microbial biopesticides" in H.D. Burges (ed), Formulation of Microbial Herbicides, Beneficial microorganisms, nematodes and seed treatments, Kluwer Academic Publishers, Dordrecht, pp. 203-233.
Sarritor, "Granular Biological Herbicide (Commercial)", Apr. 20, 2007 retrieved from internet on Dec. 9, 2008: URL: http://pr-rp.pmra-arla.gc.ca/PR_SOL/pr_web.vel?p_ukid=11869.
Written Opinion and Search Report issued in PCT/CA2008/001918 on Feb. 5, 2009.
International Preliminary Report on Patentability issued in PCT/CA2008/001918 on May 14, 2010.

* cited by examiner

*Primary Examiner* — Alton Pryor
(74) *Attorney, Agent, or Firm* — Goudreau Gage Dubuc; Julie Gauvreau

(57) ABSTRACT

Method for reducing weed on a weed-infested turfgrass. Said method comprising applying to the turfgrass an effective amount of a herbicidal fungus formulated into particles, most of the particles having a particle size of less than about 1.7 mm of diameter, whereas the herbicidal fungus decreases weed growth and/or increases weed disease development in the weed-infested turfgrass as compared to in the absence thereof; other embodiments of the methods comprising applying to the turfgrass an effective amount of a herbicidal fungus formulated into particles, and covering the weed-infested turfgrass with a ground cover sheet, whereas the herbicidal fungus and the ground cover sheet decrease weed growth and/or increases weed disease development in the weed-infested turfgrass as compared to in the absence thereof. Herbicidal fungus and kits therefore.

36 Claims, 9 Drawing Sheets

METHODS OF REDUCING WEEDS AND KITS THEREFOR

CROSS-REFERENCE TO RELATED APPLICATIONS

This application is a National Entry Application of PCT application no PCT/CA2008/001918 filed on Oct. 30, 2008 and published in English under PCT Article 21(2), which itself claims benefit of U.S. provisional application serial No. 60/983,968, filed on Oct. 31, 2007. The document above is incorporated herein in its entirety by reference.

FIELD OF THE INVENTION

The present invention is concerned with methods of reducing weeds and kits therefor.

BACKGROUND OF THE INVENTION

Weeds can be controlled/reduced by physical, cultural, chemical and biological means. Hand weeding, inter-row cultivation, chemical herbicides and encouraging the weed's natural enemies are examples of known means for controlling weeds. There remains a need for additional biological tools for controlling or reducing weed or weed growth.

The present description refers to a number of documents, the content of which is herein incorporated by reference in their entirety.

SUMMARY OF THE INVENTION

It has been surprisingly discovered that lower rates of smaller particles (e.g., 1-1.4 mm) of fungal herbicides of the present invention provide a weed reduction that is at least as good as that obtained with higher rates of larger particles. The use of lower rates (20 $g/m^2$ of weed-infested turfgrass) of smaller particles (1-1.4 mm) preserved efficient herbicidal property obtained with higher rates (40 $g/m^2$ of weed-infested turfgrass) of larger particles (1-4-2 mm) while advantageously reducing the overall cost of the process by about 50%.

It has further been surprisingly found that covering soil that has been previously treated with a fungal herbicide results in a synergistic interaction that enhances weed reduction.

The methods of the present invention may be used with any fungus having herbicidal activity. Without being so limited, such fungus include *Sclerotinia* and any other known herbicidal fungi. In specific embodiments, a *Sclerotinia* variety having herbicidal activity is used. Without being so limited, such *Sclerotinia* varieties include *Sclerotinia minor*. Without being so limited, isolates of interest includes R22, S96138, S9622, S96250 and IMI 344141 isolate deposited 26 Feb. 1991 in the International Mycological Institute.

Formulations encompassed by the present invention must maintain virulence of the herbicidal fungus, are desirably readily applied, storable, simple to prepare and use, efficient, biodegradable and of low cost. Without being so limited, useful formulations for use in the present invention include barley-based, sodium-alginate-based, kaolin clay-based formulations, millet-based formulations, rice-based formulations, and wheat-based formulations. In a specific embodiment the formulation is solid.

In accordance with the present invention, the fungus is optimally applied at rates in the range of at least about 0.2 g/plant or about 0.8 $g/m^2$ of turfgrass to about 120 $g/m^2$ of weed-infested turfgrass and in a specific embodiment, about 0.8 $g/m^2$ to about 60 $g/m^2$ of weed-infested turfgrass. As used herein, the measure $g/m^2$ refers to the weight of the fungus-containing particles in grams per square meter of weed-infested turfgrass. When an amount as low as 0.8-1.6 $g/m^2$ of weed-infested turfgrass is used, the herbicidal fungus formulation is desirably not applied homogenously on the weed-infested turfgrass but is instead applied specifically on weeds. The term "plant" in the expression "g/plant" refers to the weed sought to be reduced or controlled and not to other plants on the turfgrass. Below this minimum range, no significant effect is generally observed and above this range, although no deleterious effect is observed, no improvement was observed so that using more than 60 $g/m^2$ would generally be considered less cost-efficient. It is expected that depending on the growth habit and size of the weed, rates higher than 0.2 g/plant may be necessary for plants that are upright rather than prostrate with rosette habit.

In accordance with another aspect of the present invention, after the herbicidal fungus is applied on the weed-infested turfgrass, the ground is covered with a sheet thereby improving growth condition for the herbicidal fungus. Such sheet desirably retains water, and has a certain degree of transparency to allow some light through the fabric. Advantageously, such sheet could also be as light as possible, be re-usable and inexpensive. Without being so limited, such ground cover sheet may be made of synthetic fibres such as polyester, polyethylene and polypropylene or made of different vegetable source such as jute (including jute bags), coconut fibre, cotton, hemp or flax or a combination thereof and is typically weaved.

The ground-cover sheet/mat is typically left on the ground for about 1 to 7 days and in specific embodiment about 2-3 days. Within this period, coverage alone has no or little effect on the growth of the grass or weed. If it were left on the ground for an extended period however, namely more than 1 week, the weeds and grass would eventually be killed. Two to three consecutive days is the optimal length of time to compromise between fungal growth and environmental conditions without negatively impacting the turfgrass. During optimal spring and fall periods, the cover could be used only one day to protect the fungus from drying out on windy days or to protect it from being washed off during heavy rains. Typically in accordance with the methods of the present invention, covers are removed after 2-3 days, and by day 7 the weeds are dead or dying. Although a majority does not regrow, some large weeds may have some weak regrowth that can be reduced by a further application of the herbicidal fungus of the present invention.

More specifically, in accordance with an aspect of the present invention, there is provided A method for reducing weed on a weed-infested turfgrass comprising applying to the turfgrass an effective amount of a herbicidal fungus formulated into particles, most of the particles having a particle size of less than about 1.7 mm of diameter, whereas the herbicidal fungus decreases weed growth and/or increases weed disease development in the weed-infested turfgrass as compared to in the absence thereof.

In accordance with another aspect of the present invention, there is provided a method for reducing weed on a weed-infested turfgrass comprising applying to the turfgrass an effective amount of a herbicidal fungus formulated into particles, and covering the weed-infested turfgrass with a ground cover sheet, whereas the herbicidal fungus and the ground cover sheet decrease weed growth and/or increases weed disease development in the weed-infested turfgrass as compared to in the absence thereof.

In accordance with a further aspect of the present invention, there is provided a kit for controlling weed growth in turfgrass comprising a herbicidal fungus formulated into particles, most particles having a size between about 1 and 5 mm, and a ground cover sheet.

In a specific embodiment of the methods, the effective amount is of at least 0.8 g/m² of the weed-infested turfgrass and wherein the effective amount is applied specifically on weeds. In another specific embodiment, the effective amount is of at least 1.6 g/m² of the weed-infested turfgrass and wherein the effective amount is applied specifically on weeds. In another specific embodiment, wherein the effective amount is of at least 0.2 g/plant. In another specific embodiment, the effective amount is of at least 0.4 g/plant. In another specific embodiment, the effective amount is of at least about 10 g/m² of the weed-infested turfgrass. In another specific embodiment, the effective amount is between about 0.8 g/m² and about 120 g/m² of the weed-infested turfgrass. In another specific embodiment, the effective amount is between about 0.8 g/m² and about 60 g/m² of the weed-infested turfgrass. In another specific embodiment, the effective amount is between about 20 g/m² and about 120 g/m² of the weed-infested turfgrass. In another specific embodiment, the effective amount is between about 20 g/m² and about 30 g/m² of the weed-infested turfgrass. In another specific embodiment, the effective amount is between about 20 g/m² and about 60 g/m² of the weed-infested turfgrass. In another specific embodiment, the effective amount is between about 30 g/m² and about 120 g/m² of the weed-infested turfgrass. In another specific embodiment, the effective amount is between about 30 g/m² and about 60 g/m² of the weed-infested turfgrass. In another specific embodiment, the effective amount is between about 40 g/m² and about 120 g/m² of the weed-infested turfgrass. In another specific embodiment, the effective amount is between about 40 g/m² and about 60 g/m² of the weed-infested turfgrass. In another specific embodiment, the effective amount is between about 60 g/m² and about 120 g/m² of the weed-infested turfgrass. In another specific embodiment, the effective amount is about 20 g/m² of the weed-infested turfgrass.

In a specific embodiment of the methods or kits, most of the particles have a particle size of less than about 1.6 mm of diameter. In another specific embodiment, most of the particles have a particle size of less than about 1.5 mm of diameter. In another specific embodiment, most of the particles have a particle size of less than about 1.4 mm of diameter. In another specific embodiment, most of the particles have a particle size between about 1 mm and about 1.4 mm of diameter. In another specific embodiment, most of the particles have a particle size of less than about 1 mm.

In a specific embodiment of the methods or kits, said herbicidal fungus is a *Sclerotinia*. In another specific embodiment, said *Sclerotinia* is a *Sclerotinia minor*. In another specific embodiment, said *Sclerotinia minor* is of the IMI 344141 isolate deposited 26 Feb. 1991 in the International Mycological Institute. In another specific embodiment, said herbicidal fungus is formulated into barley-based particles. In another specific embodiment, said herbicidal fungus is formulated into sodium-alginate-based particles. In another specific embodiment, said herbicidal fungus is formulated into kaolin clay-based particles.

In a specific embodiment of the methods, said weed is broadleaf weed. In another specific embodiment, said weed is dandelion. In another specific embodiment, said weed is broadleaf plantain. In another specific embodiment, said weed is narrow leaf plantain. In another specific embodiment, said weed is ground ivy. In another specific embodiment, said weed is prostrate knotweed. In another specific embodiment, said weed is white clover.

In another specific embodiment, the methods or kits further comprises a sticking agent coated on the particles. In another specific embodiment, the sticking agent is Carrageen seaweed-based. In another specific embodiment, the sticking agent is Irish Moss Powder. In another specific embodiment, the sticking agent is *Acacia* gum.

In a specific embodiment of methods or kits, most of the particles have a particle size of less than about 5 mm of diameter. In another specific embodiment, most of the particles have a particle size of less than about 4 mm of diameter. In another specific embodiment, most of the particles have a particle size of less than about 3 mm of diameter. In another specific embodiment, most of the particles have a particle size of less than about 2 mm of diameter. In another specific embodiment, most of the particles have a particle size between about 1.4 mm and about 2 mm of diameter. In another specific embodiment, most of the particles have a particle size of less than about 1.7 mm of diameter.

In another specific embodiment of methods, said ground covering sheet comprises jute. In another specific embodiment, said ground covering sheet consists of jute. In another specific embodiment, said ground covering sheet comprises synthetic fibres.

In accordance with still a further aspect of the present invention, there is provided a herbicidal fungus formulated into particles, most of the particles having a particle size of less than about 1.7 mm of diameter.

In a specific embodiment of the herbicidal fungus, most of the particles have a particle size of less than about 1.6 mm of diameter. In another specific embodiment, most of the particles have a particle size of less than about 1.5 mm of diameter. In another specific embodiment, most of the particles have a particle size of less than about 1.4 mm of diameter. In another specific embodiment, most of the particles have a particle size between about 1 mm and about 1.4 mm of diameter. In another specific embodiment, most of the particles have a particle size of less than about 1 mm.

In another specific embodiment of the herbicidal fungus, said herbicidal fungus is a *Sclerotinia*. In another specific embodiment, said *Sclerotinia* is a *Sclerotinia minor*. In another specific embodiment, said *Sclerotinia minor* is of the IMI 344141 isolate deposited 26 Feb. 1991 in the International Mycological Institute.

In another specific embodiment of the herbicidal fungus, said herbicidal fungus is formulated into barley-based particles. In another specific embodiment, said herbicidal fungus is formulated into sodium-alginate-based particles. In another specific embodiment, said herbicidal fungus is formulated into kaolin clay-based particles. In another specific embodiment, the herbicidal fungus further comprises a sticking agent coated on the particles. In another specific embodiment, the sticking agent is Carrageen seaweed-based. In another specific embodiment, the sticking agent is Irish Moss Powder. In another specific embodiment, the sticking agent is *Acacia* gum.

As used herein, the expression "smaller particles" refers to fraction of particles wherein most of the particles have a size smaller than about 1.7 mm of diameter. In another embodiment, most of the particles have a size smaller than about 1.6 mm. In another specific embodiment, most of the particles have a size smaller than about 1.5 mm. In another specific embodiment, most of the particles have a size smaller than about 1.4 mm. In another specific embodiment, most of the particles have a size smaller than about 1.3 mm. In another specific embodiment, most of the particles have a size smaller than about 1.2 mm. In another specific embodiment, most of the particles have a size smaller than about 1.1 mm. In another specific embodiment, most of the particles have a size smaller than about 1.0 mm. In another specific embodiment, most of the particles have a size smaller than about 0.9 mm. In a more specific embodiment, most particles have a size between about 1.0 and about 1.4 mm.

As used herein, the term "powder" refers to a fraction wherein most of the particles have a size of less than about 1.0 mm.

The term "effective amount" as used herein in relation to herbicidal fungus refers to an amount sufficient to reduce weed growth and/or increase weed disease development in a weed-infested turfgrass as compared to weed growth and/or disease development in a control turfgrass (e.g., in the absence of treatment). In a specific embodiment, it refers to an amount sufficient to reduce weed growth and/or increase weed disease development in a weed-infested turfgrass of at least 10%, or of at least 20%, or of at least 30%, or of at least 40%, or of at least 50%, or of at least 60%, or of at least 70%, or at least 75%, or of at least 80%, or of at least 85%, or of at least 90% as compared to weed growth and/or disease development in a control turfgrass. In a more specific embodiment, it refers to an amount sufficient to reduce weed growth and/or increase weed disease development in a weed-infested turfgrass of at least 80% as compared to weed growth and/or disease development in a control turfgrass.

As used herein, the term "disease development" refers to the response of the weed tissues to herbicidal fungus in accordance with the present invention. More specifically it refers to any one of following symptoms on weeds: partial or complete wilting of leaves, leaves becoming chlorotic or necrotic, withering of leaves, death of leaves and any combination thereof.

As used herein the term "specifically on weeds" in relation to specific embodiments of the application of the herbicidal fungus of the present invention refers to an application on or immediately around the weeds (i.e. spot application) as opposed to a uniform application on the weed-infested turfgrass.

In the Examples herein, the term "*S. minor*" refers to the isolate *Sclerotinia minor* IMI 344141. This isolate was shown to persist about 10 days.

As used herein, the terminology "turfgrass" is meant to refer to grasses that act as a vegetation ground cover with recreational and/or aesthetic benefits for humans and serves a functional environmental purpose by preventing soil erosion.

As used herein, the term "weed-infested turfgrass" refers to turfgrass that comprises weeds of a single species or of more than one species.

As used herein, the term "SARRITOR B" refers to *S. minor* in a barley-based composition as described in Example 1 below. Unless otherwise indicated, the particle sizes of the formulation used in Examples herein is about 1.4 to about 2 mm.

As used herein the term "sticking agent" may be any known material suitable for the described purpose of aiding in the adhesion of bioherbicide particles to the surface of leaves. Without being so limited, sticking agents useful in specific embodiments of the present invention are a mix of corn syrup and water, Irish Moss Powder, *acacia* gum (AcG), an extract from carrageen seaweed (e.g., carrageen type 2 or 1), Sea-Spen™, or any combination thereof. Other sticking agents known in the art may also be used.

The efficacy of bioherbicides of the present invention is dependant on environmental conditions. The critical time is the first 7 days for the fungus to grow out of the granules and infect the weeds. Ideal conditions are a daytime temperature between 19 and 24° C., moist soils and rainfall or irrigation within 12 hours.

As used herein the term "density suppression" refers to a decrease in the number of plants, while the term "biomass reduction" refers to a visual estimate of damage to the plant. Generally, for relatively large plants, effectiveness of the herbicides of the present invention is measured in terms of density suppression while for smaller plants it is measured in terms of biomass reduction. "Ground cover" can also be used as a measure of effectiveness for plants for which density is difficult to assess. For instance, white clover is extremely difficult to measure since it produces a mat of intertwined stoloniferous plants. Ground cover is a better effectiveness measure with such plants.

As used herein, the term "weed" refers to any plant, the growth of which is desirably controlled by the methods of the present invention. Without being so limited, such weed includes dandelion, fall hawkbit, ragweed, ground ivy, prostrate knotweed, sow thistle, white clover, narrow leaf plantain (also called buckhorn plantain), broadleaf plantain, bull thistle, Canada thistle, hawkweed, speedwell, heal-all, catnip, henbit, birdsfoot trefoil, black medic, pineapple weed, common yarrow, common mallow, burdock, yellow rocket, field bindweed, fleabanes, asters, English daisy, knapweeds, mouseear chickweed, common chickweed, blueweed, oxeye daisy, chicory, Carolina false dandelion, common tansy, tansy ragwort, black medic, common vetch, yellow woodsorrel, lady's thumb, curled dock, sheep sorrel, wild strawberry, Indian mock-strawberry cinquefoil, yellow toadflax. parsleypiert, mayweed chamomile, mugwort, hawks-beard, redstem filaree, spotted spurge, *Geranium*, cudweed, spotted catsear, morningglory, purple deadnettle, pepperweed, carpetweed, field violet, yellow woodsorel, wild carrot, wild parsnip, creeping bellflower, plumeless thistle, nodding thistle, creeping buttercup, moneywort. This term excludes herein grass weeds, including wild oats, barnyard grass, annual bluegrass, crabgrass, witchgrass, foxtails, quackgrass etc., which are known not to be not harmed by the *S. minor* fungus.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
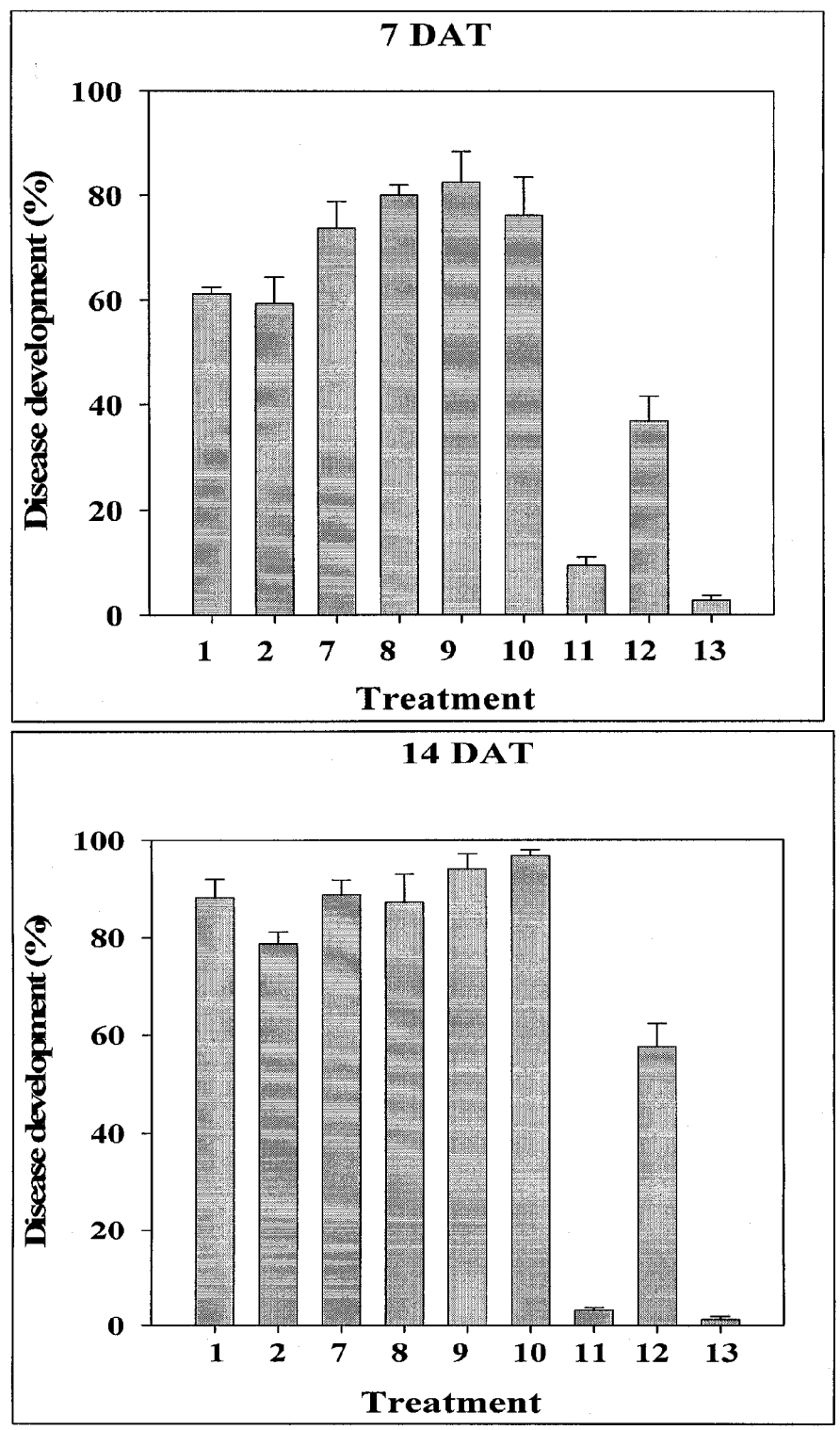
FIG. 1 is composed of two bar graphs showing the amount of disease development (biomass reduction) on dandelion from various SARRITOR B treatments 7 days after treatment (DAT) (upper panel) and 14 days after treatment (lower panel). The nature of each of treatment numbers 1, 2 and 7-13 is described in Table 6 below.

The present invention is illustrated in further details by the following non-limiting examples.

EXAMPLE 1

Herbicidal Fungus Formulations

Various formulations of *S. minor* were tested in Examples presented herein.

The barley-based formulation (SARRITOR B) was prepared as follows.

*S. minor* (IMI 344141) sclerotia (i.e. compact or hard masses of mycelium) from a stock culture were washed twice in sterile distilled water, placed in 70% ethanol for 40 seconds, transferred to a 1% hypochlorite solution for 3 min, rinsed twice with sterile distilled water, and set to dry on sterilized filter paper. The surface sterilized sclerotia were transferred aseptically onto potato dextrose agar (PDA, DIFCO Laboratories, Detroit, Mich.) plates and incubated for 4 to 5 days at 20° C./18° C. Five agar plugs (5 mm diameter), from the actively growing margin of colonies on PDA were transferred to 100 mL of a modified Richard's solution (MRS) having the following constituents L$^{-1}$: 10 g of sucrose, 10 g of KNO$_3$, 5.0 g of KH$_2$PO$_4$, 2.5 g of MgSO$_4$-7H$_2$O, 0.02 g FeCl$_3$-6H$_2$O, and 150 mL V-8 juice (Campbell Soup Company Inc.) in 250-mL Erlenmeyer flasks. Cultures were incubated for 5 days on a rotary shaker at 60 rpm at room temperature (20±1 C). The grown mycelium were collected into a sterilized blender cup (Waring Commercial, Torrington, Conn.) and homogenized gently with two 20-seconds bursts and then inoculated onto autoclaved barley (*Hordeum vulgare* L.) grits. For this, whole barley grains were ground and sieved to various diameter grits (e.g., 1-1.4 mm and 1.4-2.0 mm). Three hundred grams of barley grits were transferred into autoclavable bags with a breathable patch 44-/20.5 cm, 0.02 mm filter: 24 mm (SunBag, transparent, Sigma-Aldrich, Montreal, QC). Distilled water (210 mL) was placed into each of the bags and autoclaved at 121° C. for 20 min. After autoclaving, the bags were allowed to cool and a 15-mL of the liquid *S. minor* mycelial culture was transferred aseptically into each bag. Inoculated bags were incubated at 20° C./18° C. in the dark and shaken on the third to sixth days of incubation. The contents of each bag were then dried separately by spreading the colonized barley grits onto mesh trays for 12 h under a laminar flow. The dried inocula (aw 0.4) were placed in plastic bags (PolyBags™, 17.5-/40-7.5 cm, Gerrity Corrugated Paper Products, Concord, Oreg.) and the bags were sealed, and stored at 4° C. prior to use.

The sodium-alginate-based formulation (SARRITOR A) was prepared as follows.

*S. minor* (IMI 344141) sclerotia from a stock culture were washed twice in sterile distilled water, placed in 70% ethanol for 40 sec, transferred to 1% hypochlorite solution for 3 min, rinsed twice with sterile distilled water, and set to dry on sterilized filter paper. The surface sterilized sclerotia were transferred aseptically onto potato dextrose agar (PDA, DIFCO Laboratories, Detroit, Mich.) plates and incubated for 4 to 5 days at 20° C./18° C. Five agar plugs (5 mm diameter), from the actively growing margin of colonies on PDA were transferred to 100 mL of a modified Richard's solution (MRS) having the following constituents L$^{-1}$: 10 g of sucrose, 10 g of KNO$_3$, 5.0 g of KH$_2$PO$_4$, 2.5 g of MgSO$_4$-7H$_2$O, 0.02 g FeCl$_3$-6H$_2$O, and 150 mL V-8 juice (Campbell Soup Company Inc.) in 250-mL Erlenmeyer flasks. Cultures were incubated for 5 days on a rotary shaker at 60 rpm at room temperature (20±1 C). The grown mycelium were collected into a sterilized blender cup (Waring Commercial, Torrington, Conn.) and homogenized gently with two 20-sec bursts. Thirty g *S. minor* mycelia were combined with 100 ml filtrate (spent growth medium) in blender A and mixed for 20 sec. In a second blender (B), 450 ml distilled water, 6 g Na alginate, 6.7 g wheat bran, and 30 g kaolin were combined and mixed for 30 sec. The contents of blenders A and B were combined in a flask and swirled to mix. The mixture was dripped into 0.25 M of $CaCl_2$ forming granules. Granules were harvested, air-dried and passed through 3-mm mesh screens and collected on 2-mm mesh screens. This formulation is more costly than the two others.

The kaolin clay-based formulation (SARRITOR-K) was prepared as follows.

*S. minor* (IMI 344141) sclerotia from a stock culture were washed twice in sterile distilled water, placed in 70% ethanol for 40 sec, transferred to 1% hypochlorite solution for 3 min, rinsed twice with sterile distilled water, and set to dry on sterilized filter paper. The surface sterilized sclerotia were transferred aseptically onto potato dextrose agar (PDA, DIFCO Laboratories, Detroit, Mich.) plates and incubated for 4 to 5 days at 20° C./18° C. Five agar plugs (5 mm diameter), from the actively growing margin of colonies on PDA were transferred to 100 mL of a modified Richard's solution (MRS) having the following constituents $L^{-1}$: 10 g of sucrose, 10 g of $KNO_3$, 5.0 g of $KH_2PO_4$, 2.5 g of $MgSO_4$-$7H_2O$, 0.02 g $FeCl_3$-$6H_2O$, and 150 mL V-8 juice (Campbell Soup Company Inc.) in 250-mL Erlenmeyer flasks. Cultures were incubated for 5 days on a rotary shaker at 60 rpm at room temperature (20±1 C). The grown mycelium were collected into a sterilized blender cup (Waring Commercial, Torrington, Conn.) and homogenized gently with two 20-sec bursts. Fungal mycelia (13% final vol.) was mixed with kaolin clay (25%), soluble starch (13%), wheat bran (4%) and distilled water (45%) to form a paste. The paste was kneaded, rolled into thin sheets, and air dried. The dried sheets were ground and sieved through 3-mm and 2 mm mesh screens and collected on 1.4 mm mesh screens, or further sieved on 1.4 mm mesh screens and collected on 1 mm mesh screens. Particles sizes of 1.4 to 2 mm, and 1 to 1.4 mm, respectively, were thus obtained. A powder of <1 mm particles was obtained by sieving through a 1 mm mesh screen.

EXAMPLE 2

Effect of *Sclerotinia minor* Formulations and Application Rates on Weed Control Efficacy with Dandelion The experiment was established on Jun. 13, 1997 and Sep. 5, 1997 in a natural stand of dandelion in Ste-Anne-de-Bellevue on the Macdonald Campus of McGill University. Treatments were arranged in a randomized complete block design (i.e. standard experimental design for field trials that accounts for variation in field conditions—blocks are set up according to fertility or other factor and all treatments are included in each block) with 3 replications. Biomass reduction scores were assessed. Disease development was evaluated using a modified Horsfall-Barrett scale from 0 to 10 and expressed as percentage leaf area damaged at 1 (data not shown), 3, 7, 14, 28 and 42 days after treatment (DAT). Dandelion biomass data were recorded at 43 DAT in terms of dry weight (g/plot) (last column Tables 4-5). Temperature and precipitation were recorded at the three locations. Data were statistically analyzed with the Student-Newman-Keuls parametric and non-parametric tests. SARRITOR B (1.4-2 mm) was used without a sticking agent. Results are presented in Tables 1 and 2 below.

TABLE 1

Field Efficacy Trials with SARRITOR B and A (*Sclerotinia minor* IMI 344141) formulations - Ste-Anne-de-Bellevue, QC Jun. 13, 1997

| | Weed Control (0-100) | | | | | | Dry weight, |
|---|---|---|---|---|---|---|---|
| Treatment | 3 DAT | 7 DAT | 14 DAT | 21 DAT | 28 DAT | 42 DAT | (g/plot) |
| SARRITOR B 10 g/$m^2$ | 1.3c | 1.3e | 6.3c | 5c | 10c | 10c | 11.72ab |
| SARRITOR B 20 g/$m^2$ | 5c | 18.8c | 12.5c | 5c | 6.3c | 11.3c | 11.35ab |
| SARRITOR B 40 g/$m^2$ | 10c | 27.5c | 16.3c | 13.8c | 12.5c | 13.8c | 9.54b |
| SARRITOR B 60 g/$m^2$ | 25b | 62.5b | 36.3b | 25c | 12.5c | 15c | 7.72b |
| SARRITOR B 120 g/$m^2$ | 45a | 85a | 85a | 65b | 58.8b | 45b | 4.97c |
| SARRITOR A 20 g/$m^2$ | 0c | 12.5c | 11.3c | 10c | 8.8c | 21.3c | 7.38b |
| SARRITOR A 40 g/$m^2$ | 1.3c | 16.3c | 5c | 13.8c | 7.5c | 13.8c | 9.44b |
| SARRITOR A 60 g/$m^2$ | 3.8c | 15c | 2.5c | 20c | 2.5c | 21.7c | 10.9b |
| Killex ™* | 6.3c | 53.8b | 92.5a | 87.5a | 72.5a | 81.7a | 3.98c |
| Barley 120 g/$m^2$ | 0c | 0e | 0c | 0c | 0c | 0c | 14.25a |
| Na Alginate 60 g/$m^2$ | 0c | 0e | 0c | 0c | 0c | 0c | 15a |

*Killex ™ - 1.7 kg ai/ha; 0.6% solution applied at 200 ml/$m^2$. Means followed by a common letter in the same column are not significantly different at the 5% level.
Weather conditions: June (at application day): T avg = 19.5 C: T max = 24.2 C; Min = 16.3 C (no precipitation - very dry).

TABLE 2

Field Efficacy Trials with SARRITOR B and A (*Sclerotinia minor* IMI 344141) formulations - Ste-Anne-de-Bellevue, QC, Sep. 5, 1997

| | Weed Control (0-100) | | | | | | Dry weight |
|---|---|---|---|---|---|---|---|
| Treatment | 3 DAT | 7 DAT | 14 DAT | 21 DAT | 28 DAT | 42 DAT | (g/plot) |
| SARRITOR B 10 g/$m^2$ | 32.5b | 45b | 48.8bc | 38.8b | 33.8e | 38.8de | 0.87ab |
| SARRITOR B 20 g/$m^2$ | 43.8b | 61.3b | 46.3bc | 52.5b | 47.5e | 50be | 0.71b |

TABLE 2-continued

Field Efficacy Trials with SARRITOR B and A (*Sclerotinia minor* IMI 344141) formulations - Ste-Anne-de-Bellevue, QC, Sep. 5, 1997

| Treatment | Weed Control (0-100) | | | | | | Dry weight (g/plot) |
|---|---|---|---|---|---|---|---|
| | 3 DAT | 7 DAT | 14 DAT | 21 DAT | 28 DAT | 42 DAT | |
| SARRITOR B 40 g/m$^2$ | 73.8a | 91.3a | 85b | 75a | 67.5d | 75ac | 0.29c |
| SARRITOR B 60 g/m$^2$ | 88.8a | 95a | 88.8b | 88.3a | 80b | 77.5ac | 0.15c |
| SARRITOR B 120 g/m$^2$ | 91.3a | 100a | 100a | 96.3a | 95a | 90a | 0.05d |
| SARRITOR K 20 g/m$^2$ | 32.5b | 37.5b | 37.5c | 40b | 42.5e | 36.3de | 1.38ab |
| SARRITOR K 60 g/m$^2$ | 70a | 86.3a | 78.8b | 77.5a | 72.5c | 73.8ac | 0.40c |
| SARRITOR K 80 g/m$^2$ | 73.8a | 96.3a | 90b | 88.8a | 77.5bc | 81.3ac | 0.29c |
| Killex* | 25b | 43.8b | 46.3bc | 45b | 47.5e | 60bc | 1.23ab |
| barley 120 g/m$^2$ | 0c | 0c | 0d | 0c | 0f | 0f | 2.18a |
| kaolin 80 g/m$^2$ | 0c | 0c | 0d | 0c | 0f | 0f | 2.02a |

*Killex ™ - 1.7 kg ai/ha; 0.6% solution applied at 200 ml/m$^2$. Means followed by a common letter in the same column are not significantly different at the 5% level.
Weather conditions: on application day: T avg = 14.5 C: T max = 22.8 C; Min= 8.3 C (rain 2 days after application).

It appears that optimal reduction is generally obtained on DAT 7 with Sarritor B treatments. Dandelion plants die within 3-7 days after treatment. Lower scores after 7 days are due to some regrowth, and new weed growth from seed germination. To obtain optimal results, environment conditions must be appropriate and in order to kill weeds that are well established with a strong tap root (about 8 leaf stage of dandelion), the application is optimally repeated on dandelions that regrow. The difference of results for the same application rates are due to weather conditions which was too dry in June and good in September. From these results it may be seen that the three different formulations (B,K,A) performed similarly and weed control was rate dependent.

In these experiments, rates of 40 g/m$^2$ and above provided optimal weed control. Although it is usually understood that 80% reduction is the minimum threshold for an agent to be designated a herbicide, a rate able to decrease weed growth or increase disease development as compared to a control in weed is useful for the present invention.

EXAMPLE 3

Effect of a Sticking Agent on Disease Development and Growth Reduction of Dandelion Plants by the *Sclerotinia minor* Barley-Based Formulation This experiment was established in September, 2002 in a natural stand of dandelion infested turfgrass to determine whether or not a sticking agent, (carageenan-based), improved the efficacy of the *Sclerotinia minor* formulation (SARRITOR B, 1.4-2.0 mm). The study was arranged in a completely random design with 3 replicates of 3 treatments; SARRITOR B at 60 $g/m^2$, SARRITOR B at 60 $g/m^2$ amended with Carageenan, and untreated control. Control plots were treated with autoclaved barley grits at 60 $g/m^2$. The sticking agent used was Irish moss powder (i.e. a type of Carageenan available from BioServ, USA) and was applied prior to drying to the surface of SARRITOR B colonized barley grits. Each plot was 1 $m^2$ in which a 0.25 $m^2$ area was treated. Disease development (i.e. Biomass reduction) was evaluated using a modified Horsfall-Barrett scale and expressed as percentage of damaged leaf area.

TABLE 3

Effect of a sticking agent (Carageenan) on biological efficacy of *Sclerotinia minor*

| Treatment | Disease development (mean ± SE %) on sampling day 7 DAT(Sep. 30) | 27 DAT (Oct. 17) |
|---|---|---|
| 60 $g/m^2$ | 76.9 ± 7.4a | 90.0 ± 4.6a |
| 60 $g/m^2$ + sticker | 92.0 ± 3.5a | 98.9 ± 0.7a |
| Control | 0b | 0b |

Means followed by the same letter in the same column do not differ significantly ($P > 0.05$) as determined by Tukey's multiple range test.

Although there are no statistical difference between treatments, less variability in disease development especially 7 DAT after inoculation was observed in treatment where SARRITOR B was amended with Carageenan.

EXAMPLE 4

Effect of *Sclerotinia minor* Granules Rate on Weed Control Efficacy with Dandelion This experiment was designed to determine the effect of reduced rates of SARRITOR B (1.4-2 mm) on weed control efficacy on dandelion (*Taraxacum officinale*).

The trial was set up on Jun. 4, 2004 on a natural stand of dandelion infested turfgrass on the Macdonald Campus of McGill University, Ste-Anne-de-Bellevue, QC. Experimental design was a randomized complete block with two replicates of 24 treatments: 1=SARRITOR B applied at 15 $g/m^2$; 2=SARRITOR B applied at 20 $g/m^2$; 3=SARRITOR B at 25 $g/m^2$; 4=SARRITOR B at 30 $g/m^2$; 5=SARRITOR B at 35 $g/m^2$; 6=SARRITOR B at 40 $g/m^2$; 7=SARRITOR B applied at 15 $g/m^2$+fertilizer (3.8 g/0.25 $m^2$ of 27-3-4) 8=SARRITOR applied at 20 $g/m^2$+fertilizer; 9=SARRITOR B at 25 $g/m^2$+fertilizer; 10=SARRITOR B at 30 $g/m^2$+fertilizer; 11=SARRITOR B at 35 $g/m^2$+fertilizer; 12=SARRITOR B at 40 $g/m^2$+fertilizer; 13=SARRITOR B applied at 15 $g/m^2$+grass seeds (2.6 g/0.25 $m^2$); 14=SARRITOR B applied at 20 $g/m^2$+grass seeds; 15=SARRITOR B at 25 $g/m^2$+grass seeds; 16=SARRITOR B at 30 $g/m^2$+grass seeds; 17=SARRITOR B at 35 $g/m^2$+grass seeds; 18=SARRITOR B at 40 $g/m^2$+grass seeds; 19=untreated control; 20=Killex™ at 1.7 kg a.i./ha; 21=untreated control+fertilizer; 22=Killex™+fertilizer; 23=untreated control+seeds; 24=Killex™+seeds. Each plot was 1 $m^2$ (1 m×1 m) in which a 0.25 $m^2$ area was treated.

Disease development was evaluated using a modified Horsfall-Barrett scale from 0 to 10 and expressed as percentage leaf area damaged (biomass reduction). No sticking agent was used.

TABLE 4

Effect of combination of SARRITOR B with fertilizer or turfgrass seeds on weed control efficacy

| Treatment | Application rate$^a$ (g/m$^2$) | Fertilizer$^b$ | Turfgrass seeds$^c$ | Mean biomass reduction$^{e*}$ (%) 11 DAT | 21 DAT |
|---|---|---|---|---|---|
| 1 | 15 | | | 13.7 | 35.0 |
| 2 | 20 | | | 21.2 | 30.0 |
| 3 | 25 | | | 26.2 | 42.5 |
| 4 | 30 | | | 51.2 | 55.0 |
| 5 | 35 | | | 40 | 50.0 |
| 6 | 40 | | | 61.2 | 67.5 |
| 7 | Killex 1$^d$ | | | 72.5 | 90.0 |
| 8 | Control 1 | | | — | — |
| 9 | 15 | + | | 11.2 | 22.5 |
| 10 | 20 | + | | 16.2 | 32.5 |
| 11 | 25 | + | | 27.5 | 52.5 |
| 12 | 30 | + | | 41.2 | 60.0 |
| 13 | 35 | + | | 40.0 | 57.5 |
| 14 | 40 | + | | 60.0 | 55.0 |
| 15 | Killex 2 | + | | 85.0 | 87.5 |
| 16 | Control 2 | + | | — | — |
| 17 | 15 | | + | 21.2 | missing |
| 18 | 20 | | + | 18.7 | 35.0 |
| 19 | 25 | | + | 27.5 | 40.0 |
| 20 | 30 | | + | 43.7 | 55.0 |
| 21 | 35 | | + | 42.5 | 57.5 |
| 22 | 40 | | + | 52.5 | 80.0 |
| 23 | Killex 3 | | + | 96.2 | 96.0 |
| 24 | Control 3 | | + | — | — |

*as compared to the untreated control
$^a$= 1 m$^2$ plot with 0.25 m$^2$ inoculation zone
$^b$= lawn fertilizer at 3.8 g/0.25 m$^2$
$^c$= turf grass seed mixture at 2.6 g/0.25 m$^2$
$^d$= Killex 0.6% solution applied at 200 ml/m$^2$
$^e$= dandelion biomass reduction (plot level) in comparison with respective control

EXAMPLE 5

Effect of Application Rates and of Sticking Agents on the Efficacy of *Sclerotinia minor* Granules on Dandelion The experiment was established on Jun. 21, 2004 in a natural stand of dandelion in Ste-Anne-de-Bellevue on the Macdonald Campus of McGill University. The experiment was arranged in a completely random design with 3 replicates of 8 treatments: 1=SARRITOR B (1.4-2 mm diam) applied at 20 g/m$^2$; 2=SARRITOR B at 30 g/m$^2$; 3=SARRITOR B at 40 g/m$^2$; 4=SARRITOR B at 20 g/m$^2$ plus sticking agent; 5=SARRITOR B at 30 g/m$^2$ plus sticking agent; 6=SARRITOR B at 40 g/m$^2$ plus sticking agent; 7=untreated control; 8=Killex™ at 1.7 kg a.i./ha rate. The sticking agent, Irish moss powder (BioServ, USA) was applied prior to drying to the surface of SARRITOR B colonized barley grits. Each plot was 1 m$^2$ (1 m×1 m) in which a 0.25 m$^2$ area was treated. Disease development was evaluated using a modified Horsfall-Barrett scale from 0 to 10 and expressed as percentage leaf area damaged (biomass reduction).

TABLE 5

Reduced dose-response experiment with sticking agent

Weed Control = Mean leaf area diseased/damaged (Biomass reduction) (% ± SE) compared to the untreated control

| Treatment | 2 DAT | 4 DAT | 8 DAT | 14 DAT |
|---|---|---|---|---|
| SARRITOR B 20 g/m$^2$ | 15.0 ± 7.6 | 36.7 ± 12.0 | 53.3 ± 8.8 | 58.3 ± 3.3 |
| 20 g/m$^2$ + sticking agent | 30.0 ± 5.8 | 46.7 ± 10.1 | 53.3 ± 12.0 | 58.3 ± 4.4 |
| SARRITOR B 30 g/m$^2$ | 10.7 ± 6.7 | 35.3 ± 4.4 | 46.7 ± 8.8 | 60 ± 7.6 |
| 30 g/m$^2$ + sticking agent | 15.8 ± 5.8 | 45.0 ± 3.2 | 45.3 ± 10.9 | 55 ± 2.9 |
| SARRITOR B 40 g/m$^2$ | 21.7 ± 3.3 | 58.3 ± 4.4 | 70 ± 5.8 | 68.3 ± 7.3 |
| 40 g/m$^2$ + sticking agent | 27.5 ± 4.3 | 58.3 ± 6.0 | 70 ± 0.0 | 73.3 ± 4.4 |
| Untreated control | 0 | 0 | 0 | 0 |
| Killex ™ (1.7 kg ai/ha) | 7.3 ± 1.4 | 29.0 ± 18.4 | 81.7 ± 10.9 | 85 ± 5.8 |

In Examples 4 and 5 above, the 40 g/m$^2$ rate reduced dandelion biomass by 70% (Tables 1 and 2). At 20 g/m$^2$, biomass of dandelion (*Taraxacum officinale*) was reduced by 60% (Table 2). Table 5 shows that the sticking agent accelerates weed control, especially at lower rates of application.

EXAMPLE 6

Effect of *Sclerotinia minor* Particle Size, a Sticker, Production Media, and Rate on Dandelion Control Efficacy Various treatments described in Table 6 below were applied on turfgrass to determine the effect of SARRITOR B particle size, (1.0-1.4 mm diam cf 1.4-2.0 mm diam) the addition of a sticking agent, the effect of oxalic levels in inoculum production, and the rate of application on biomass reduction of dandelion. The fungus release oxalic acid during invasion of weed plant tissues decreasing the pH and thus promoting polygalacturonase and other tissue lysing enzymes. SARRITOR B treatments were compared to an untreated control (check), the standard chemical herbicide (KILLEX™) and an organic control option (beet juice extract). Experiments were initiated on Sep. 22, 2004. No rain occurred during the 5 days after application, however, abundant dew presented on turfgrass. Relative humidity from midnight to 7 am was: 86.1% (September 22), 91.6% (September 23) and 98.5% (September 24). Disease development was evaluated using a modified Horsfall-Barrett scale from 0 to 10 and expressed as percentage leaf area damaged (Biomass reduction).

TABLE 6

Dose-response experiment with various parameters

| Treatment | Biomass reduction (%) compared to the untreated control | | | |
|---|---|---|---|---|
| | 5 DAT | 7 DAT | 14 DAT | 21 DAT |
| 1. Sarritor 20 g/m$^2$ | 55.6abc | 61.3b | 88.3abc | 88.1abc |
| 2. Sarritor 20 g/m$^2$ + sticker$^1$ | 36.3bcde | 59.4b | 78.8abc | 75.0bc |
| 3. Sarritor 30 g/m$^2$ | 71.9a | 80.0ab | 98.5a | 96.0a |
| 4. Sarritor 30 g/m$^2$ + sticker | 78.8a | 85.0a | 92.5abc | 90.6ab |
| 5. Sarritor 40 g/m$^2$ | 78.8a | 90.0a | 98.0a | 98.5a |

TABLE 6-continued

Dose-response experiment with various parameters

| Treatment | Biomass reduction (%) compared to the untreated control | | | |
|---|---|---|---|---|
| | 5 DAT | 7 DAT | 14 DAT | 21 DAT |
| 6. Sarritor 40 g/m² + sticker | 77.5a | 90.0a | 96.3ab | 97.0a |
| 7. Sarritor 20 g/m² (1-1.4)² | 66.3a | 73.8ab | 88.8abc | 89.8abc |
| 8. Sarritor 20 g/m² Oxalic #7³ | 65.0ab | 80.0ab | 87.3abc | 90.5ab |
| 9. Sarritor 20 g/m² Oxalic #1³ | 67.5a | 82.5a | 94.0abc | 95.0a |
| 10. Sarritor 20 g/m² (1-1.4)² + sticker | 51.9abcd | 76.3ab | 96.8abc | 98.0a |
| 11. Beet Juice⁴ | 24.4de | 9.4d | 3.3b | 2.8d |
| 12. Killex (2,4-D + MCPP + Dicamba)⁵ | 31.3cde | 36.9c | 57.5abc | 73.8c |
| 13. Untreated control | 7.3e | 2.8d | 1.3c | 4.3d |

* data within a column flanked with a common letter means that they are not significantly different according to the Tukey test at α = 0.05.
1 = dry powder of Irish moss (Bio-Serv, Frenchtown, NJ, USA)
2 = 1-1.4 mm
3 = oxalic acid #1 (SM mycelia produced on MRS media); oxalic acid #7 (SM mycelia produced on sucrose solution (SUS): 25 g sucrose, 10 g soy hydrolysate, 5 g $KH_2PO_4$, 2.5 mg $MgSO_4$ * 7 $H_2O$, 1000 ml distilled water).
4 = Beet juice applied at 40 ml/m²
5 = KILLEX-0.6% solution applied at 200 ml/m²

Selected results from Table 6 are also presented in FIG. 1.

Overall, the smaller sized particles (1.0-1.4 mm) rate treatments (20 g/m²) performed very well by day 14 and the level of disease control was maintained beyond 21 DAT with disease development ranges from 80 to 100. These results demonstrated that the SARRITOR B smaller particles (1.0-1.4 mm) product provides an effective weed control at 20 g/m² that is not statistically different from that obtained with the 1.4-2 mm size at a rate of 40 g/m² resulting in a 50% reduction in quantity of *Sclerotinia minor* used. The cost is thus reduced since the end users will be able to use less product to treat the same number of weeds. Decreasing the particle size from 1.4-2.0 mm to 1.0-1.4 mm reduces the costs by approximately 50%.

EXAMPLE 7

Effect of *Sclerotinia minor* Particle Size on Weed Control Efficacy with Dandelion This experiment was conducted on a natural stand of dandelion in a turf area from May 24th to Jun. 16, 2005. The SARRITOR B formulation was applied as colonized barley grits, which were separated into three particle size fractions: (1) 1 to 1.4 mm; (2) 1.4 to 2 mm; (3) a powder having particle sizes less than 1 mm, using standard soil sieves.

Completely randomized block design with 4 blocks/replications of 7 treatments. Experimental plots were 0.5 m×0.5 m. Five model dandelion plants were marked within each plot using wooden golf tees. Only the model dandelions were observed for disease severity.

Dandelion biomass reduction was evaluated 3, 7, 14 and 23 days after treatment (DAT) using a modified Horsfall-Barrett scale from 0 to 10 and expressed as percentage leaf area damaged. Table 7 below shows the main meteorological data collected from the local meteorological station for May 24 to May 30.

TABLE 7

| Meteorological data. | | | | | | | | | |
|---|---|---|---|---|---|---|---|---|---|
| | Temperature, ° C. | | | Relative Humidity, % | | | Precipitation | Wind max | |
| Date | Min | Max | Aver | Min | Max | Aver | (mm) | (km/h) |
| 24-May | 9.3 | 17.3 | 13 | 51 | 77 | 64.5 | 0 | 28 |
| 25-May | 9 | 20.5 | 15 | 32 | 77 | 49.8 | 0 | 26 |
| 26-May | 9.6 | 13.4 | 11.5 | 48 | 87 | 67.1 | 0.8 | 28 |
| 27-May | 10.9 | 13.1 | 11.7 | 73 | 99 | 86.5 | 4.4 | 19 |
| 28-May | 10.5 | 22.4 | 15.5 | 42 | 100 | 79.4 | 1.4 | 13 |
| 29-May | 8.3 | 20.4 | 14.4 | 55 | 100 | 84.7 | 0.4 | 19 |
| 30-May | 12.3 | 19.7 | 15.2 | 64 | 88 | 81.3 | 1.2 | 19 |

May 24 = application date

Plots were fertilized 6 days prior to the inoculation (May 18th) using N-P-K (28-3-6) fertilizer. Plots were mowed prior to the inoculation and then two weeks after the inoculation. Plots were not irrigated prior to inoculation, but the field was irrigated on June 4th and June 16th in the morning for 2 hours. The results are shown in Table 8 below.

TABLE 8

| Effect of different treatments on dandelion biomass and density reduction. | | | | |
|---|---|---|---|---|
| | Dandelion biomass reduction (%) as compared to control | | | |
| | Days after treatment | | | |
| Treatment ($g/m^2$) | 3 | 7 | 14 | 23 |
| Untreated control | 0 | 0 | 0 | 0 |
| 20 g (powder < 1 mm) | 0.6a[1] | 1.1e | 15.0b | 47.2b |
| 20 g (1-1.4 mm) | 0.6a | 47.5bc | 83.1a | 93.7a |
| 20 g (1.4-2 mm) | 0.7a | 18.9d | 81.6a | 51.5b |
| 30 g (1.4-2 mm) | 1.2a | 55b | 91.9a | 93.7a |
| 40 g (1.4-2 mm) | 1.7a | 75.6a | 100a | 87.5a |
| Killex[2] | 3.7a | 31.2cd | 81.2a | 71.8a |

[1]Within a column, biomass reduction means represented by common letters are not significantly different according to Tukey Range test at $\alpha = 0.05$.
[2]Killex ™ rate: 1.7 kg ai/ha; 0.6% solution applied at 200 $ml/m^2$.

Application rate. At 7 DAT, there were no significant differences between the SARRITOR B formulation applied either at 20 $g/m^2$ (smaller particle size of 1-1.4 mm) or at 30 $g/m^2$ (particle size of 1.4 to 2 mm) or Killex™ treatment. At 14 DAT, all tested SARRITOR B application rates were as effective as Killex™ treatment except when SARRITOR B was applied as a powder formulation at 20 $g/m^2$. SARRITOR B applied at 20 $g/m^2$ (particles of 1-1.4 mm) or 30 $g/m^2$ and 40 $g/m^2$ (particles of 1.4-2 mm) resulted in significant dandelion density reduction 14 DAT (Table 8). By 23 DAT, no significant difference in dandelion biomass reduction was found among all tested treatments except when SARRITOR B was applied as particles of 1.4 to 2 mm or as a powder formulation at 20 $g/m^2$.

Particle size. SARRITOR B formulated as 1 to 1.4 mm particle size was equal to or superior to SARRITOR B formulated as 1.4 to 2 mm particles at any tested rate or as SARRITOR B powder formulation in terms of level of dandelion suppression.

EXAMPLE 8

Effect of *Sclerotinia minor* in Combination with Textile Covering on Weed Control Efficacy with Dandelion and other Broadleaf Weeds The experiment was started on the 15 Aug. 2005 in a turfgrass area where the maximum temperature during the week of application was about 30° C. The grass was covered after application of SARRITOR B, 1.4-2.0 mm. The cover cloth was a horticultural textile made of natural jute fiber (available from TerraTex, Lenrod Industries Ltd, Aleggett & Plett Company, Ville Saint Laurent, Quebec). The treatments were 10, 20, 30, 40 g/m$^2$ of SARRITOR B formulation in addition to untreated control. No sticking agent was used. The plot area was 40×40 cm (0.16 m$^2$) with three replications and a completely randomized design. The plots received 2 h daily irrigation by sprinkler in the first three days after application. Assessments were conducted on the day before application, and one, two and three weeks post application. The measured parameters were the number of dandelion per plot (density suppression) and broadleaf weeds groundcover percentage.

Figure 2:
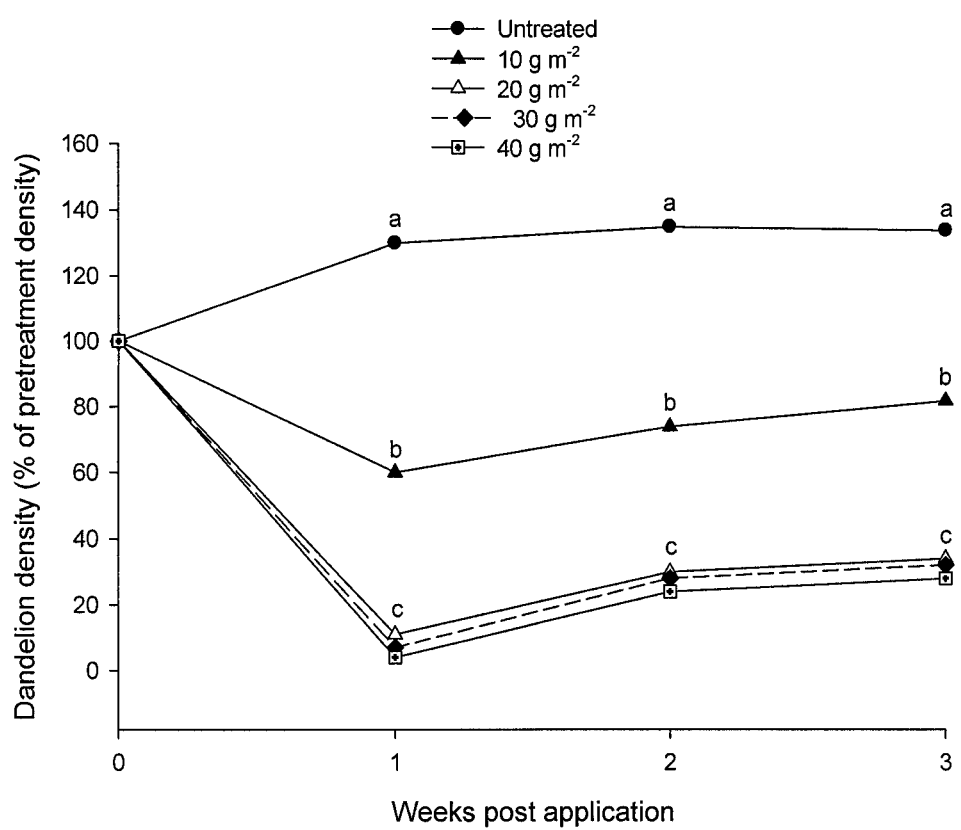
FIG. 2 is a graph showing the effect of different rates of application of a barley-based formulation of the *Sclerotinia minor* IMI 344141 isolate in combination with jute coverage on dandelion density (calculated as % of pretreated value). All plots were covered by a fabric textile made of natural jute for three consecutive days after application and received irrigation of 2 h day$^{-1}$. Within each time assessment, means with a common letter are not significantly different at P=0.05 according to Tukey's test.
Figure 3:
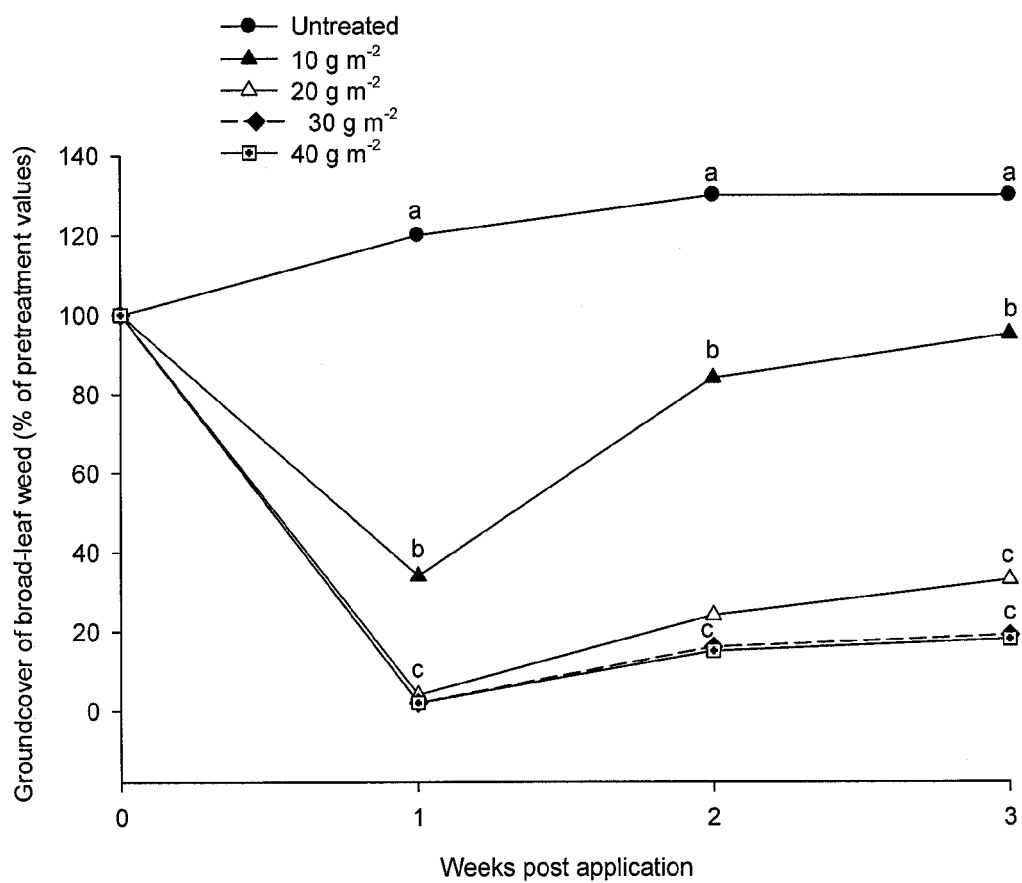
FIG. 3 is a graph showing the effect of the rate of applying a barley-based formulation of the *Sclerotinia minor* IMI 344141 isolate in combination with jute coverage on groundcover percentage of all broadleaf weeds (i.e. dicotyledon weeds) growth (calculated as % of pretreated value); All plots were covered by a fabric textile made of natural jute for three consecutive days after application and received irrigation of 2 h day$^{-1}$. Within each time assessment, means with a common letter are not significantly different at P=0.05 according to Tukey's test.

FIGS. 2 and 3 show the resulting data. A rate of application as low as 20 g/m$^2$ followed by jute covering yielded efficient dandelion density suppression (% of untreated) and decreased broadleaf weed groundcover.

EXAMPLE 9

Effect of *Sclerotinia minor* in Combination with Textile Covering on Weed Control Efficacy with Prostrate Knotweed This experiment was designed to study the effect of *S. minor* barley-based formulation (SARRITOR B, 1.4-2.0 mm) without a sticking agent on newly emerged prostrate knotweed (*Polygonum aviculare*) with and without jute covering.

The experiment was started on May 12, 2006. Prior to application, it had rained for 10 h. During the application, there was light rain followed by 3 days of light rain and cloudy humid conditions. Temperatures varied between 10 and 16° C. The plots had a surface of 0.1 m$^2$, four of which were treated at a rate of 60 g/m$^2$ and four were left untreated in a completely randomized design. Covers were removed after 3 days.

Figure 4:
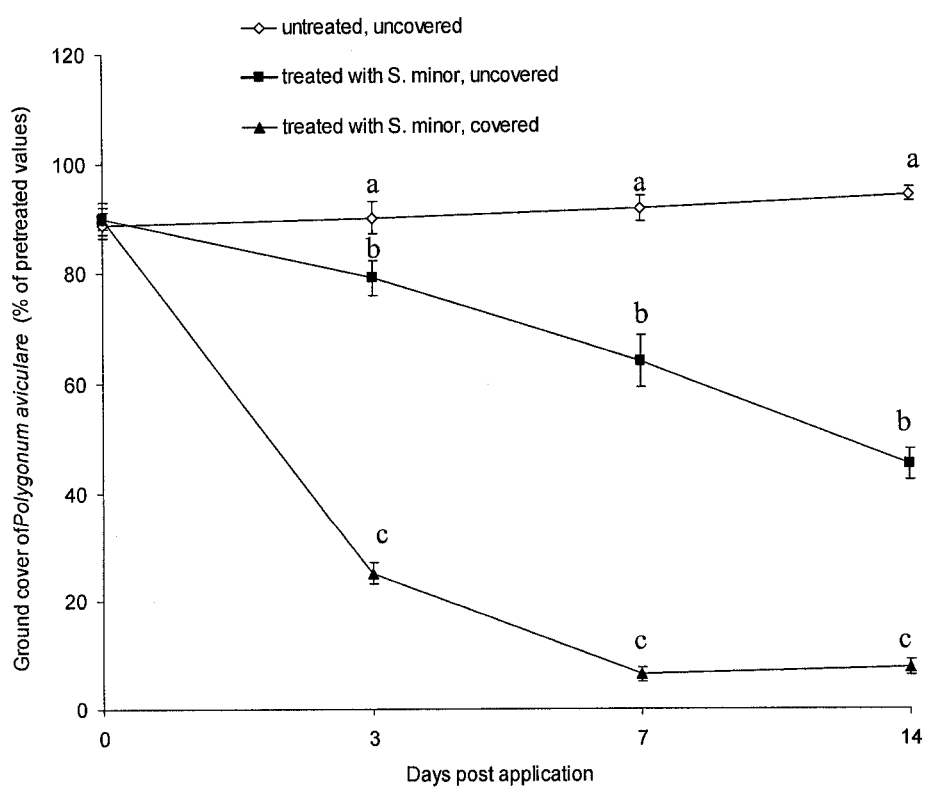
FIG. 4 is a graph showing the effect of a barley-based formulation (60 g m$^{-2}$) of *Sclerotinia minor* IMI 344141 isolate in combination with jute coverage on newly emerged prostrate knotweed (*Polygonum aviculare*) growth. A fabric textile made of natural jute was used to cover plots for three consecutive days after application. Error bars refer to standard errors at each time assessment. Within each time assessment, means with a common letter are not significantly different at P=0.05 according to Tukey's test.

As may be seen in FIG. 4, treating the plots with jute covering in addition to the *S. minor* formulation dramatically decreased the ground cover of prostrate knotweed as compared to the untreated plot and the treated uncovered plot.

EXAMPLE 10

Effect of *Sclerotinia minor* Lower Application Rates in Combination with Textile Covering on Weed Control Efficacy with Prostrate Knotweed This experiment was designed to study the effect of different rates of application of *S. minor* SARRITOR B (1.4-2.0 mm) formulation without a sticking agent on prostrate knotweed ground cover with or without jute covering.

The experiment was started on Jun. 1, 2006. There was no rainfall on the first two days of application but light rainfall prevailed during the second night and third day. The temperature was close to 20° C. The plots had a surface of 0.2 m$^2$. Three replications were conducted in a randomized complete block design with the following treatments: 1) UN: untreated and not covered; 2) UC: untreated and covered; 3) T20N: treated (20 g/m$^2$) and not covered; 4) T30N: treated (30 g/m$^2$) and not covered; 5) T40N: treated (40 g/m$^2$) and not covered; 6) T20C: treated (20 g/m$^2$) covered; 7) T30C: treated (30 g/m$^2$) covered; and 8) T40C: treated (40 g/m$^2$) covered. Covers were removed after 3 days.

Figure 5:
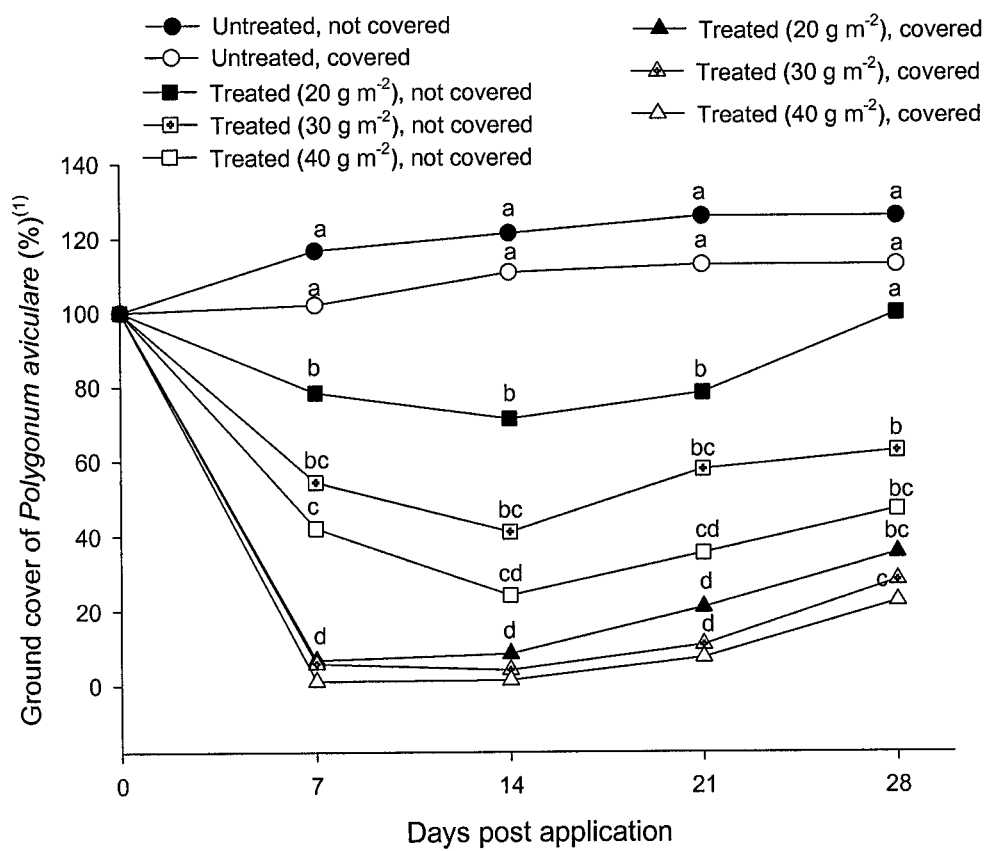
FIG. 5 is a graph showing the effect of different rates of application of a barley-based formulation of the *Sclerotinia minor* IMI 344141 isolate with or without jute covering on prostrate knotweed (*Polygonum aviculare*) growth in turfgrass. At each time, means with a common letter are not significantly different at P=0.05 according to Tukey's test. (1) Calculated as a percentage of the pre-treatment groundcover values.

As may be seen in FIG. 5, for all rates of application, combined treatment of the SARRITOR B formulation and covering resulted in a dramatic decrease of prostrate knotweed ground covering.

EXAMPLE 11

Effect of *Sclerotinia minor* Application Rates in Combination with Textile Covering on Weed Control Efficacy with Broadleaf Plantain This experiment was designed to study the effect of different rates of application of SARRITOR B, 1.4-2.0 mm formulation without a sticking agent on broad leaf plantain density with or without jute covering.

The experiment was started on Jun. 8, 2006. There was very light rainfall on the day of application, which prevailed during the first night and second day. The temperature range was 12-20° C. The plots had a surface area of 0.2 m$^2$. Covers were removed after 3 days. Three replications were conducted in a randomized complete block design with the treatments shown in Table 9 below.

TABLE 9

Effect of different combinations of application rates of SARRITOR B formulation with or without jute fabric covering to control broadleaf plantain in turfgrass

| | Number of plants per plot area (0.2 m$^2$) Weeks post application | | | | |
|---|---|---|---|---|---|
| Treatment | Pre application | 1 | 2 | 3 | 4 |
| Untreated uncovered | 7 | 7 | 7 | 8 | 8 |
| Untreated covered | 6 | 6 | 6 | 6 | 6 |
| uncovered treated 20 g m$^{-2}$ | 8 | 4 | 3 | 2 | 3 |
| Uncovered treated 30 g m$^{-2}$ | 5 | 1 | 1 | 1 | 2 |
| uncovered treated 40 g m$^{-2}$ | 6 | 1 | 0 | 0 | 0 |
| covered treated 20 g m$^{-2}$ | 8 | 1 | 0 | 0 | 0 |
| Covered treated 30 g m$^{-2}$ | 7 | 1 | 1 | 0 | 0 |
| Covered treated 40 g m$^{-2}$ | 7 | 0 | 0 | 0 | 0 |

Table 9 shows that, once again, jute covering after treatment with the *S. minor* formulation yielded the highest broadleaf plantain density suppression.

EXAMPLE 12

Effect of *Sclerotinia minor* Application Rates in Combination with Textile Covering on Weed Control Efficacy with Narrow Leaf Plantain This experiment was designed to study the effect of different rates of application of *S. minor* barley-based formulation (SARRITOR B, 1.4-2.0 mm) without a sticking agent on narrow leaf plantain (Plantago lanceolate) density with or without jute covering.

The experiment was started on Jun., 19$^{th}$2006. There was very light rainfall on the day of application, a good amount of rainfall during the first night and second day which was cloudy and had a temperature of 24° C. There was rainfall on the third day followed by four sunny days (26-28° C.). The plots had a surface area of 0.2 m². Covers were removed after 3 days. Three replications were conducted in a randomized complete block design with the treatments shown in Table 10 below.

TABLE 10

Effect of different combinations of application rates of SARRITOR B formulation with or without jute fabric covering to control narrow leaf plantain in turfgrass.

| Treatment | Number of plants per plot area (0.2 m²) (density suppression) Weeks post application | | | | |
|---|---|---|---|---|---|
| | Pre application | 1 | 2 | 3 | 4 |
| Untreated uncovered | 11.7 | 12 | 14 | 9 | 11.7 |
| Untreated covered | 11.7 | 9 | 14 | 12 | 11.7 |
| uncovered treated 20 g m$^{-2}$ | 12.3 | 11 | 12 | 9 | 10.7 |
| Uncovered treated 30 g m$^{-2}$ | 8.7 | 10 | 8 | 7 | 8.3 |
| uncovered treated 40 g m$^{-2}$ | 10.7 | 10 | 6 | 11 | 9.0 |
| covered treated 20 g m$^{-2}$ | 8.7 | 6 | 4 | 2 | 4.0 |
| Covered treated 30 g m$^{-2}$ | 8.3 | 3 | 4 | 2 | 3.0 |
| Covered treated 40 g m$^{-2}$ | 13.7 | 4 | 6 | 4 | 4.7 |

Table 10 shows that jute covering after treatment with the *S. minor* formulation yielded the highest narrow leaf plantain density suppression.

EXAMPLE 13

Effect of *Sclerotinia minor* Application Rates in Combination with Textile Covering on Weed Control Efficacy with White Clover This experiment was designed to study the effect of different rates of application of *S. minor* barley-based formulation (SARRITOR B, 1.4-2.0 mm) without a sticking agent on the percentage of ground cover with white clover (*Trifolium repens*) with or without jute covering. Percentage of ground cover was used as a measure of effectiveness in this case instead of density because density of white clover is extremely difficult to measure since it produces a mat of intertwined stoloniferous plants.

The experiment was started on May 1, 2006. There was no rainfall on the day of application nor during the second day. Light rainfall prevailed during the second night and third day. The plots had a surface area of 0.2 m². Covers were removed after 3 days. Three replications were conducted in a randomized complete block design with the treatments shown in Table 11.

TABLE 11

Effect of different combinations of application rates of SARRITOR B formulation with or without jute fabric covering to control white clover in turfgrass.

| Treatment | Ground cover (%) Weeks post application | | | | |
|---|---|---|---|---|---|
| | Pre application | 1 | 2 | 3 | 4 |
| Untreated uncovered | 92 | 93 | 95 | 95 | 95 |
| Untreated covered | 87 | 88 | 88 | 93 | 92 |
| uncovered treated 20 g m$^{-2}$ | 88 | 72 | 60 | 73 | 90 |
| Uncovered treated 30 g m$^{-2}$ | 90 | 45 | 53 | 57 | 67 |
| uncovered treated 40 g m$^{-2}$ | 97 | 30 | 25 | 43 | 60 |
| covered treated 20 g m$^{-2}$ | 93 | 15 | 13 | 30 | 43 |
| Covered treated 30 g m$^{-2}$ | 92 | 4 | 8 | 18 | 25 |
| Covered treated 40 g m$^{-2}$ | 97 | 2 | 7 | 13 | 30 |

Table 11 shows that jute covering after treatment with the *S. minor* formulation yielded the highest white clover density suppression.

EXAMPLE 14

Effect of *Sclerotinia minor* Application Rates in Combination with Textile Covering on Weed Control Efficacy with Ground Ivy This experiment was designed to study the effect of different rates of application of SARRITOR B, 1.4-2.0 mm without a sticking agent on the percentage of ground cover with ground ivy (*Glechoma hederacea*) with and without jute covering.

The experiment was started on May 1, 2006. There was no rainfall on the day of application nor during the second. Light rainfall prevailed during the second night and third day. The plots had a surface area of 0.2 m². Covers were removed after 3 days. Three replications were conducted in a randomized complete block design with the treatments shown in Table 12 below.

TABLE 12

Effect of different combinations of application rates of *S. minor* IMI 344141 isolate barley-based formulation with or without jute fabric covering to control ground ivy in turfgrass.

| Treatment | Ground cover (%) visually estimated for each plot Weeks post application | | | | |
|---|---|---|---|---|---|
| | Pre application | 1 | 2 | 3 | 4 |
| Untreated uncovered | 75 | 83 | 87 | 95 | 95 |
| Untreated covered | 72 | 75 | 80 | 87 | 90 |
| uncovered treated 20 g m$^{-2}$ | 55 | 37 | 32 | 47 | 60 |
| Uncovered treated 30 g m$^{-2}$ | 68 | 47 | 38 | 42 | 52 |
| uncovered treated 40 g m$^{-2}$ | 68 | 28 | 15 | 22 | 28 |
| covered treated 20 g m$^{-2}$ | 65 | 28 | 17 | 17 | 23 |

TABLE 12-continued

Effect of different combinations of application rates of S. minor IMI 344141 isolate barley-based formulation with or without jute fabric covering to control ground ivy in turfgrass.

| Treatment | Ground cover (%) visually estimated for each plot Weeks post application | | | | |
|---|---|---|---|---|---|
| | Pre application | 1 | 2 | 3 | 4 |
| Covered treated 30 g m$^{-2}$ | 82 | 7 | 7 | 10 | 22 |
| Covered treated 40 g m$^{-2}$ | 75 | 4 | 2 | 6 | 12 |

Table 12 shows that jute covering after treatment with the *S. minor* formulation yielded the highest white clover density suppression.

EXAMPLE 15

Effect of Jute Covering on Above and Belowground of Turfgrass Biomass with or without Treatment of *Sclerotinia minor*

The experiment was a completely randomized design with 6 treatment levels and three replications and conducted twice through time, in June 2006 and August 2007. Twenty four potting trays (25×20×6 cm) were filled with a mixture of ½ pasteurized black soil, ¼ sand and ¼ pro-mix (Premier Pro-mix™, Premier Horticulture Ltee, Riviere-du-Loup, QC). The grass seeds were sown in a rate of 3 g per tray (~the recommended sowing rate under field conditions). The grass seeds used in this experiment were from a commercial grass seed mixture [30% *Poa pratensis* L. (Kentucky bluegrass), 40% *Festuca rubra* L. var. *rubra* s.l. (creeping red fescue) and 30% *Lolium perenne* L. (turf type perennial ryegrass), C.I.L.® Golfgreen™, Brantford, ON]. After three weeks of growth, 18 out of the 24 pots were chosen to be used for the experiment based on similarities of grass vigour.

The trays were placed in a greenhouse at 24±2° C. with 15 hr of light/day at photon flux density minimum of 350±50 μ mol m$^{-2}$s$^{-1}$. The SARRITOR B *S. minor* colonized barley granules (1.4-2 mm diameter) were applied at 3 g per tray (~60 g m$^{-2}$) on the surface of the pre moistened soil. The trays were uncovered or covered for 3 or 5 days of two folds of jute fabric (EXTRA TEXT™, LENORD Industries LTD, St-Laurent, QC). The trays were checked daily and misted with water whenever needed. One week after the treatment application, the top ground grass biomass of each tray was clipped with hedge shears (PlantSmart™, Wal*Mart, Montreal, QC, Canada), while the belowground biomass was left without irrigation for three further days then the whole soil with roots of each tray was squashed and rolled on a screen with 2 mm mesh size until all dry soil was removed. The roots then carefully washed from soil residues using a wide mouth container filled with water. The above and belowground biomass of each tray was separately placed in paper bags, oven dried at 80° C. for 72 h, and then weighed. The data from both repeats were pooled, and then subjected to Levene test of SAS (SAS Institute, Cary, N.C., 2002) to test for homogeneity of error variances. Data from both repeats were combined as error variances were homogeneous. The main treatment effect was determined using ANOVA of SAS (SAS Institute Inc., Cary, N.C., 2002).

Figure 6:
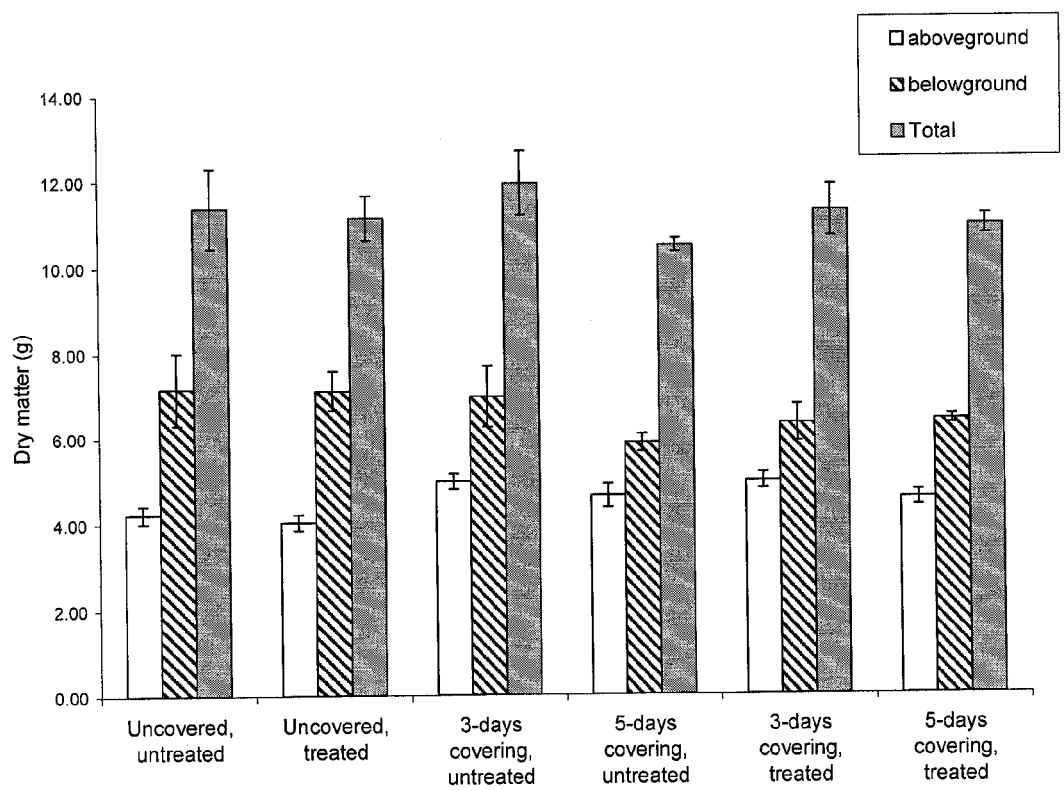
FIG. 6 is a graph showing the effect on above ground, belowground or total biomass of commercial turfgrass due to 3 or 5 days of jute covering with or without a barley-based formulation of the *Sclerotinia minor* IMI 344141 isolate (60 g m$^{-2}$). Error bars represent the standard errors of three replications.

As can be observed on FIG. 6, no significant effect was obtained on aboveground, belowground or total biomass of commercial turfgrass due to 3 or 5 days of covering with jute under both *S. minor* treated or untreated plots (FIG. 6).

EXAMPLE 16

Effect of Different Covers on the Efficacy of *Sclerotinia minor* to Control all Broadleaf Weeds Present in Turfgrass This experiment was conducted 31 Jul. 2007. The experiment was conducted in extreme weather conditions of high temperature to explore the maximum effect expected from different covers in comparison to uncovered treatments and also to know the maximum effect of covers on turfgrass. A temperature and relative humidity data logger was setup on the surface of the turf at the field study site. During the three days of covering, the maximum, minimum and average temperatures were 32, 16 and 26° C., consecutively. The maximum daily temperatures for the three days were 31, 33 and 32° C. while the minimum temperatures were 22, 16 and 21° C. During the three days of covering, the maximum, minimum, and average prevalent relative humidities (RH) were 100, 51 and 77%, respectively.

The experiment was conducted on the Macdonald Campus of McGill University in Ste-Anne-de-Bellevue. The grass sward was approximately 90% Kentucky bluegrass and 10% of red fescue. At the time of application, the field was highly infested with white clover, *Trifolium repens* followed by dandelion, *Taraxacum officinale* and broadleaf plantain, *Plantago major*.

The experiment was designed in split plot, the main plot was cover types and the sub plots were *S. minor* rates. The experiment was conducted in four replications with a plot area of 0.4×0.4=0.16 m$^2$. There were five levels of the cover factor: (1) uncovered, (2) covered with jute burlap cloth, (3) covered with a black thick polyester fabric (textile) used commercially in agriculture as groundcover to control weeds, (4) white transparent polyester row cover fabric and (5) a black plastic made of polyethylene. There were four rates of barley-based *S. minor* (1.4-2 mm) compared: (1) untreated, (2) treated with 20 g m$^{-2}$, (3) treated with 40 g m$^{-2}$; and (4) treated with 60 g m$^{-2}$ of *S. minor* barley-based formulation. The whole field was sprinkler irrigated for 2 hrs a day. One fold of sheet was used.

While no negative impacts on turfgrass were observed from the jute and the white fabric, the polyethylene fabric caused damage for all covered areas with no correlation to *S. minor* application rate. However, the grass was able to recover after 2-3 weeks. The black fabric caused some damage to the top 2-5 cm of the grass leaves; but the grass recovered directly after the first mowing (one week post application) (Data not shown).

Jute cloth and black fabric alone had neither positive nor negative effect on broadleaf weeds; however the polyethylene sheet significantly decreased broadleaf weed groundcover in the first week after the treatment (FIG. 7A). Surprisingly, the white fabric caused a significant increase in broadleaf weeds after application (FIG. 7A).

Figure 7:
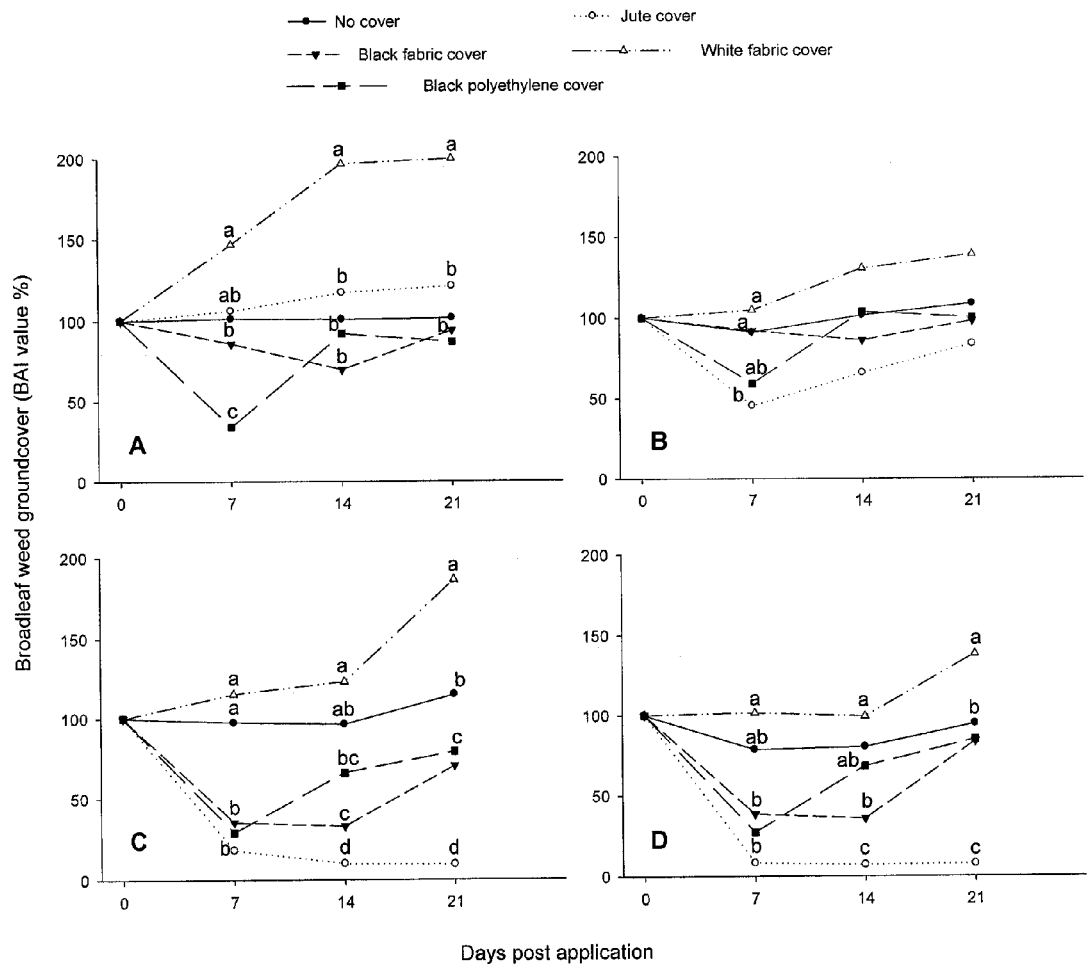
FIG. 7 is a graph showing the effect of different rates of a barley-based formulation of the *Sclerotinia minor* IMI 344141 isolate in combination with different covers on all broadleaf weeds (i.e. dicotyledon weeds) growth in turfgrass. The covers were jute burlap, a black polyester ground cover, white polyester row cover and a black polyethylene cover. All plots were covered for up to three consecutive days after application. (A) No *S. minor* was applied (B) 20 g m$^{-2}$ (C) 40 g m$^{-2}$ and (D) 60 g m$^{-2}$ of *S. minor* barley-based formulation. Within each graph means with a common letter at each time are not significantly different at P=0.05 according to Tukey's test. Treatments application was initiated under extreme weather conditions of high temperature (~32° C.)
Figure 8:
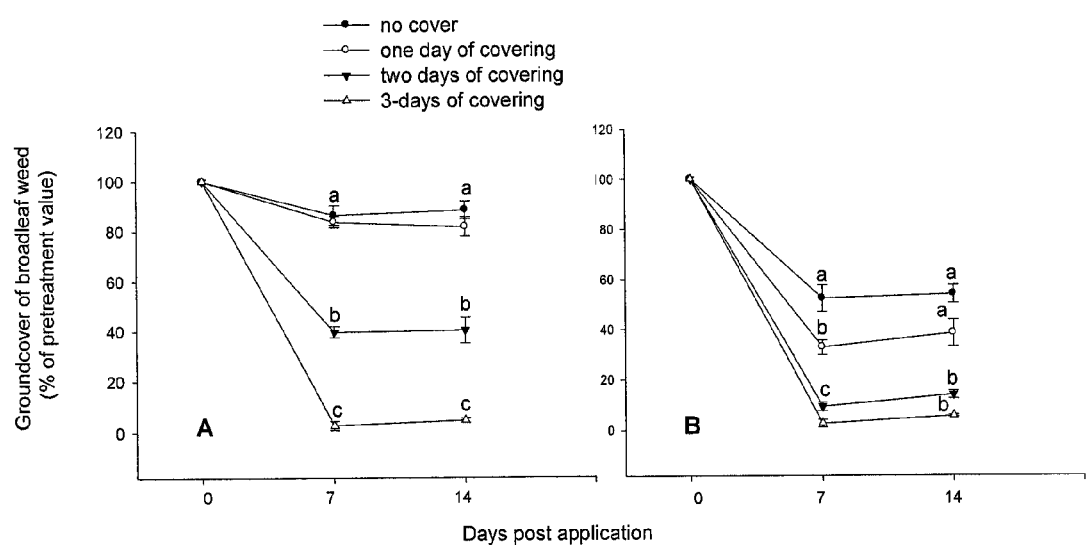
FIG. 8 is a graph showing the effect of the number of days of jute covering on the efficacy of a barley-based formulation of the *Sclerotinia minor* IMI 344141 isolate to control all broadleaf weeds (i.e. dicotyledon weeds) in turfgrass. (A) July 2007 trial (B) August 2007 trial. *S. minor* rates were 40 g m$^{-2}$ of barley based formulation. Within each graph means with a common letter at each time are not significantly different at P=0.05 according to Tukey's test. Values are means of four replicates and error bars refer to standard errors of the means.
Figure 9:
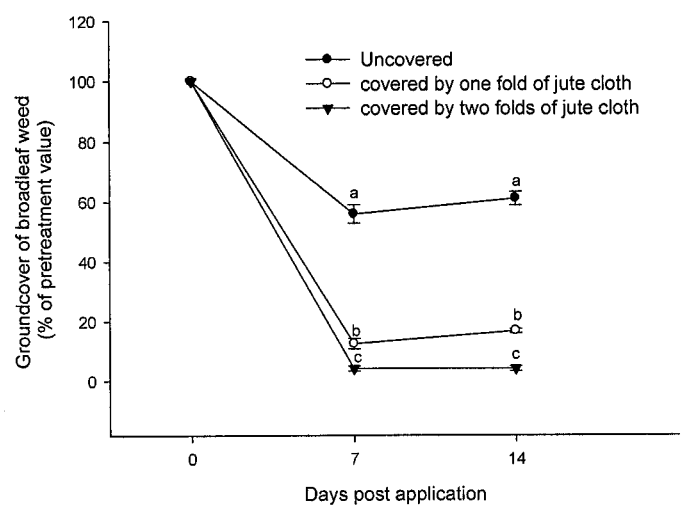
FIG. 9 is a graph showing the effect of the number of folding layers of jute covering on the efficacy of a barley-based formulation of the *Sclerotinia minor* IMI 344141 isolate to control all broadleaf weeds (i.e. dicotyledon weeds) in turfgrass. *S. minor* rates were 40 g m$^{-2}$ of barley based formulation. Means with a common letter at each time are not significantly different at P=0.05 according to Tukey's test. Values are means of six replicates and error bars refer to standard errors of the means.

At a rate of 20 g m$^{-2}$ of *S. minor* barley based formulation (FIG. 7 B), there were no significant differences between the different covers except at seven days after application when the jute and polyethylene covers caused around 50% control while other covers provided less control. 40 and 60 g m$^{-2}$ treatments (Figure C and D, respectively) caused similar efficacy for almost all covers but covering by jute caused the best control of broadleaf weeds all over the study period with a constant reduction to about 95%. This was significantly different from other covers at 14 and 21 days after application. The no cover treatment showed very limited control of broadleaf weeds with Sarritor B due to high temperature which severely inhibited growth of the fungus (FIG. 7 C-D).

EXAMPLE 17

Effect of Number of Days of Jute Covering on the Efficacy of *Sclerotinia minor* to Control all Broadleaf Weeds Present in Turfgrass Experiments date: Trial-1: late July 2007 and trial-2: late August 2007. Weather conditions: In order to determine the least number of days of jute covering needed to maximize the efficacy of *S. minor* to control broadleaf weeds and to know if weather conditions can interact with the number of days of covering, two field trials were conducted. The first trial in late July was conducted during extremely high temperature (maximum daily temperatures for the three days were 31, 33 and 32 C while the minimum temperatures were 22, 16 and 21 C). The second trial in late August was conducted under cooler weather conditions with 20° C. the maximum daily temperature.

The study site: The experiment was conducted on the Macdonald Campus of McGill University in Ste-Anne-de-Bellevue. The grass sward was approximately 90% of Kentucky bluegrass and 10% of red fescue. At the time of application, the field was highly infested with white clover, *Trifolium repens* followed by dandelion, *Taraxacum officinale* and broadleaf plantain, *Plantago major*.

Experimental design: Both experiments were a completely randomized design with one factor and four replications. The studied factor was the number of days of covering by jute after applying a rate of 40 g $m^{-2}$ of *S. minor* barley-based formulation (1.4-2 mm). Four treatment levels were applied: (1) 0-days (uncovered); (2) 1-day; (3) 2-days and (4) 3-days of covering by jute cloth. The plot area was 0.4×0.4=0.16 $m^2$. The field site was sprinkler irrigated for 2 hrs a day.

Results: Although the prevalent weather conditions for both trials were not the best for *S. minor* activity to cause damage to broadleaf weeds without the help of jute covering, the conditions during the second trial were more close to the optimum growth conditions of *S. minor*. However the *S. minor* growth conditions are a combination of temperature and moisture and also the lasting duration of these optimum conditions and this generally can be achieved only in late May and late September. Therefore, the no cover treatments in late July (FIG. 8A) provide no control while the late August trial (FIG. 8B) provided limited control (~50%) of broadleaf weeds. The results of two trials were not combined as Levene's test indicated heterogeneity of variances. In the first trial, the effect of one day of covering is negligible, while two days covering significantly increased broadleaf control, but three days of covering was needed to cause significantly more control attaining 95% control. As the weather was cooler in the $2^{nd}$ trial, two days of covering caused similar effect as the three days of jute covering indicating the interaction of weather factors and days of covering on efficacy of *S. minor*.

EXAMPLE 18

Effect of Number of Folds of Jute Covering on the Efficacy of *Sclerotinia minor* to Control all Broadleaf Weeds Present in Turfgrass Two trials were conducted in different locations in late August 2007. The experiment was conducted on the Macdonald Campus of McGill University in Ste-Anne-de-Bellevue. The grass sward was approximately 90% of Kentucky bluegrass and 10% of red fescue. At the time of application, the field was highly infested with white clover, *Trifolium repens* followed by dandelion, *Taraxacum officinale* and broadleaf plantain, *Plantago major*.

Experimental design: Both experiments were completely randomized designs with one factor and three replications. The studied factor was the number of folds of jute covering after applying a rate of 40 g $m^{-2}$ of *S. minor* barley-based formulation (1.4-2 mm). Three treatment levels were applied: (1) 0-folds (uncovered); (2) 1-fold; (3) 2-folds of jute cloth. The plot area was 0.4×0.4=0.16 $m^2$. The whole field was sprinkler irrigated for 2 hrs a day. Covers were removed after three days.

Results: The results of the two trials are homogeneous according to Levene's test so the results were combined and analyzed as one experiment of six replicates. The prevalent weather conditions were not the best for *S. minor* activity to cause damage of broadleaf weeds without the aid of jute covering. Therefore, as expected, the no cover treatment showed limited control (~45%) of broadleaf weeds (FIG. 9). One and two folds of jute covering gave similar levels of control (90-95%) which were significantly greater control compared with the uncovered plots with *S. minor* (FIG. 9). Unfortunately no experiment was conducted during very hot conditions (i.e. July or early August) since two folds may be necessary to retain more moisture and increase the efficacy of *S. minor* on broadleaf weed control during periods of high temperature.

EXAMPLE 19

Effect of Application Rates and Particle Sizes on the Efficacy of *Sclerotinia minor* to Control Dandelion Plants in Turfgrass The experiment started Sep. 19, 2007. It used a completely randomized design consisting of 7 replicated treatments.

Six fractions of the Sarritor B *S. minor* barley-based formulation were prepared using the Canadian standard soil sieves as described in Table 16 below. The experimental site was a turfgrass field located in the Avian Conservation Centre (Macdonald Campus of McGill University). At the beginning of the experiment, the dandelion plants were at 4-to-6-leaf stage. The disease severity and regrowth on dandelion plants was assessed 7, 10, 14 and 21 days after treatment (DAT). The Sarritor B particles quality (vigour test) was estimated prior to field application and represented as mycelia growth rate on PDA plates (mm/24 h and 48 h) (See Table 16 below). The meteorological data was collected from the local meteorological station located in vicinity with the experimental field in Saint-Anne-de-Bellevue (Quebec) and was as described in Table 13 below. The grass was mowed on day 14 DAT to a 7 cm height.

TABLE 13

Temperature at Saint-Ann-de-Bellevue meteorological station

| DATE | Temperature, ° C. | | | Total Rain |
|---|---|---|---|---|
| September | Max | Min | Mean | mm |
| 20 | 24.5 | 14.2 | 19.4 | 0 |
| 21 | 25.3 | 11.5 | 18.4 | 0 |
| 22 | 28.2 | 15.1 | 21.7 | 0 |
| 23 | 22.4 | 11.3 | 16.9 | 0 |
| 24 | 25.5 | 10.7 | 18.1 | 0 |
| 25 | 29.3 | 16.1 | 22.7 | Trace |
| 26 | 26.5 | 17.6 | 22.1 | 3 |
| 27 | 17.8 | 13.1 | 15.5 | 14.4 |
| 28 | 20.1 | 10.4 | 15.3 | 4.4 |
| 29 | 17.3 | 6.8 | 12.1 | 0 |

TABLE 13-continued

Temperature at Saint-Ann-de-Bellevue meteorological station

| DATE | Temperature, ° C. | | | Total Rain |
|---|---|---|---|---|
| 30 | 18.4 | 5.9 | 12.2 | 0 |
| Mean | 23.2 | 12.1 | 17.7 | |
| October | | | | |
| 1 | 21.2 | 12.2 | 16.7 | 0 |
| 2 | 20.8 | 13.1 | 17 | 0 |
| 3 | 25.6 | 16.3 | 21 | 0 |
| 4 | 23.3 | 12.5 | 17.9 | 0 |
| 5 | 25.1 | 10.4 | 17.8 | 0 |
| 6 | 17.6 | 9.1 | 13.4 | 4.2 |
| 7 | 14.5 | 7.2 | 10.9 | 4.4 |
| 8 | 12.6 | 6.7 | 9.7 | 7.8 |
| 9 | 13.6 | 4.3 | 9 | Trace |
| 10 | 16.4 | 10.2 | 13.3 | 0 |
| 11 | 13.5 | 10.6 | 12.1 | 1.4 |
| Mean | 18.6 | 10.2 | 14.4 | |

The treatments applied were: 1=0.2 g/plant (1.4-2 mm); 2=0.2 g/plant (1-1.4 mm); 3=0.2 g/plant (0.8-4 mm)—Sarritor B prior to its to its separation in the various fractions used in examples herein (i.e. barley substrate is ground to 4 mm or less, autoclaved, cooled, inoculated with *S. minor*; allowed to grow out in breathable bags and dried) ; 4=0.4 g/plant (1.4-2 mm); 5=0.4 g/plant (1-1.4 mm); 6=0.4 g/plant (0.8-4 mm)—Sarritor B prior to its separation in the various fractions used in examples herein; 7=untreated control. Each treatment was applied on 0.5 m×0.5 m plot with 5-7 model dandelion plants marked with a golf tee within each plot. Only specifically marked plants were observed for disease severity; each treatment was replicated 3 times. Results are presented in Table 14 below. Assuming 400 weeds per 100m$^2$ (general accepted standard for Canadian lawn care industry), 0.2-0.4 g per plant represents about 0.8-1.6 g/m$^2$.

TABLE 14

Mean disease severity and plant regrowth

| Treatment* | Rate (g/plant) | Biomass reduction, % (±SE) on sampling date | | | | Plant regrowth 21 DAT (%± SE) |
|---|---|---|---|---|---|---|
| | | 7 DAT | 10 DAT | 14 DAT | 21 DAT | |
| 1.4-2 mm | 0.2 | 68.7 ± 6.3a | 90.8 ± 2.4a | 98.7 ± 1.3a | 97.3 ± 1.4a | 26.7 ± 17.6 |
| 1-1.4 mm | 0.2 | 58.6 ± 6.6a | 82.7 ± 4.3a | 96.7 ± 1.9a | 98.0 ± 0.7a | 40.0 ± 0.0 |
| 0.8-4 mm | 0.2 | 67.5 ± 7.5a | 71.5 ± 8.1a | 92.3 ± 3.6a | 96.7 +− 2.2a | 33.3 ± 13.3 |
| 1.4-2 mm | 0.4 | 61.2 ± 4.9a | 85.3 ± 3.7a | 99.2 ± 0.8a | 97.7 ± 0.7a | 46.7 ± 6.7 |
| 1-1.4 mm | 0.4 | 70.5 ± 5.6a | 89.2 ± 3.3a | 97.7 ± 2.3a | 96.5 ± 0.7a | 68.3 ± 9.3 |
| 0.8-4 mm | 0.4 | 48.5 ± 7.7a | 75.5 ± 5.3a | 93.6 ± 3.4a | 99.1 ± 0.6a | 15.0 ± 7.6 |
| Control | | 2.3 ± 1.2 | 4.8 ± 1.3 | 3.5 ± 1.3 | 5 ± 1.4 | n/a |

*Within a column and at a specific application rate, means with a common letters are not significantly different at α = 0.05

Results

Plant regrowth corresponds to the number of treated plants that regrow after being severely damaged by Sarritor B. It was measured by visual count of new leaves from root crown. Plant regrowth was observed 21 DAT and ranged from 15 to 68% on different treatments (see Table 14 above).

Based on grit size, the Sarritor's granular formulation could be divided into 6 fractions (see Table 15 below). About 50% of the grits particles have a size of about 1.4 to 2 mm.

TABLE 15

Sarritor's fraction (size and weight)

| Reps | 1 D > 4 mm | 2 4 mm > D > 2 mm | 3 2 mm > D > 1.4 mm | 4 1.4 mm > D > 1 mm | 5 1 mm > D > 0.8 mm | 6 D < 0.8 mm |
|---|---|---|---|---|---|---|
| 1 | 5.63 | 28.9 | 51.43 | 12.24 | 2.55 | 2.13 |
| 2 | 1.83 | 26.14 | 49.91 | 14.77 | 5.31 | 1.91 |
| 3 | 1.91 | 26.85 | 47.06 | 15.19 | 5.89 | 2.06 |
| 4 | 3.46 | 27.56 | 43.98 | 15.55 | 6.03 | 2.31 |
| 5 | 2.73 | 27.24 | 48.42 | 13.71 | 4.38 | 2.51 |
| Total *(g) | 15.56 | 136.69 | 240.8 | 71.46 | 24.16 | 10.92 |
| Percent | 3.1 | 27.3 | 48.2 | 14.3 | 4.8 | 2.2 |

*sample = 100 g

Vigour is a measure of the health of the fungus *S. minor* on the barley substrate. Vigour is the radial growth of *Sclerotinia* on Potato Dextrose Agar (PDA) plates and generally correlates positively to the development of disease on the weeds and killing the weeds—i.e. higher vigour start to grow faster and quicker on artificial medium. Higher vigour imparts greater survivability of the inoculum in storage. The vigour of different Sarritor's fractions ranged from 4.8 to 15.3 mm (24 h) and from 21.3 to 48.6 mm (48 h) with a tendency of higher growth rates from the bigger fractions (see Table 16 below). Table 14 showed however that the smaller particles are equally effective in killing weeds (disease severity over 80% represents optimal damage to kill the weed). The large particles will be effective, however these results show that the smaller particles are effective.

TABLE 16

Mycelial radial growth (Vigour) of various Sarritor's fractions, mm

| | 24 h | | | | 48 h | | | |
|---|---|---|---|---|---|---|---|---|
| Treatments* | II (1-1.4) | I (1.4-2.0) | III (2-4.0) | IV (0.8-4.0) | II (1-1.4) | I (1.4-2.0) | III (2-4.0) | IV (0.8-4.0) |
| 1 | 3.7 | 17.7 | 17.9 | 17.4 | 21 | 49.2 | 49.1 | 43.1 |
| 2 | 0 | 15.3 | 12.7 | 13.1 | 15.8 | 39.1 | 45.3 | 32.1 |
| 3 | 11.4 | 10.1 | 20.2 | 17.3 | 44.2 | 28.2 | 55.6 | 49.6 |
| 4 | 3.1 | 0 | 12.5 | 14.9 | 16.7 | 19.8 | 53.7 | 45.5 |
| 5 | 7.1 | 11.7 | 14.4 | | 27.1 | 35.8 | 52.7 | |
| 6 | 0 | 8.4 | 13.3 | | 8.2 | 26.4 | 49.3 | |
| 7 | 7.6 | 16.9 | 22.1 | | 34.8 | 41.3 | 59.8 | |
| 8 | 0 | 0 | 16.4 | | 9.7 | 13.5 | 48.7 | |
| 9 | 9.9 | 14.4 | 13.9 | | 32.4 | 31.6 | 43.8 | |
| 10 | 5.5 | 7.7 | 16.7 | | 6.3 | 27.6 | 51.4 | |
| 11 | 12.8 | 7.2 | 14.4 | | 30.8 | 32.7 | 35.3 | |
| 12 | 0 | 4.4 | 10.1 | | 17.6 | 27.1 | 39.2 | |
| 13 | 11.2 | 15.4 | 17 | | 37.1 | 38.1 | 46.5 | |
| 14 | 4.9 | 6.2 | 13.1 | | 21.9 | 36.4 | 48.2 | |
| 15 | 0 | 13.1 | 16.1 | | 9.9 | 37.8 | 44.2 | |
| 16 | 0 | 5.2 | 11.3 | | 0 | 29.8 | 39.8 | |
| 17 | 10.7 | 10.1 | 17.8 | | 34.1 | 33.9 | 47.2 | |
| 18 | 0 | 0 | 14.2 | | 0 | 17.8 | 49.2 | |
| 19 | 8.9 | 14.1 | 16.4 | | 31.2 | 42.1 | 59 | |
| 20 | 0 | 0 | 14.5 | | 27.7 | 21.7 | 53.9 | |
| Mean | 4.8 | 8.9 | 15.3 | 15.7 | 21.3 | 31.5 | 48.6 | 42.6 |
| L = 0.05 | b | b | a | | b | b | a | |

*Within a column and at a specific application rate, means with a common letters are not significantly different at $\alpha = 0.05$ Although the present invention has been described hereinabove by way of specific embodiments thereof, it can be modified, without departing from the spirit and nature of the subject invention as defined in the appended claims.

The invention claimed is:

1. A method for reducing weed on a weed-infested turfgrass comprising applying to the turfgrass an effective amount of a *Sclerotinia* formulated into particles, wherein the effective amount is between about 20 g/m² and about 60 g/m² of the weed-infested turfgrass, most of the particles having a particle size of less than or about 1.7 mm of diameter, whereby the *Sclerotinia* decreases weed growth and/or increases weed disease development in the weed-infested turfgrass as compared to in the absence thereof.

2. The method of claim 1, wherein the effective amount is:
   (a) between about 20 g/m² and about 30 g/m² of the weed-infested turfgrass;
   (b) between about 30 g/m² and about 60 g/m² of the weed-infested turfgrass;
   (c) between about 40 g/m² and about 60 g/m² of the weed-infested turfgrass; or
   (d) about 20 g/m² of the weed-infested turfgrass.

3. The method of claim 1, wherein most of the particles have a particle size of:
   (a) less than or about 1.6 mm of diameter;
   (b) less than or about 1.5 mm of diameter;
   (c) less than or about 1.4 mm of diameter;
   (d) between about 1 mm and about 1.4 mm of diameter; or
   (e) less than or about 1 mm.

4. The method of claim 1, wherein said *Sclerotinia* is a *Sclerotinia minor*.

5. The method of claim 4, wherein said *Sclerotinia minor* is of the IMI 344141 isolate deposited 26 Feb. 1991 in the International Mycological Institute.

6. The method of claim 1, wherein said *Sclerotinia* is formulated into:
   (a) barley-based, millet-based, rice-based or wheat-based particles;
   (b) sodium-alginate-based particles; or
   (c) kaolin clay-based particles.

7. The method of claim 1, wherein said weed is:
   (a) broadleaf weed;
   (b) dandelion;
   (c) broadleaf plantain;
   (d) narrow leaf plantain;
   (e) ground ivy;
   (f) prostrate knotweed; or
   (g) white clover.

8. The method of claim 1, further comprising a sticking agent coated on the particles.

9. The method of claim 8, wherein the sticking agent is:
   (a) Carrageen seaweed-based;
   (b) Irish Moss Powder; or
   (c) Acacia gum.

10. The method of claim 6, wherein said *Sclerotinia* is formulated into barley-based particles.

11. A method for reducing weed on a weed-infested turfgrass comprising:
   (1) applying to the turfgrass an effective amount of a *Sclerotinia* formulated into particles; wherein most of the particles have a particle size of less than about 5 mm of diameter; and wherein the effective amount is of:
  (a) at least 0.8 g/m² of the weed-infested turfgrass and wherein the effective amount is applied on weeds;
  (b) at least 0.2 g/plant; or
  (c) at least or about 10 g/m² of the weed-infested turfgrass; and
(2) covering the weed-infested turfgrass with a ground cover sheet for about 1 to 7 days, whereby the *Sclerotinia* and the ground cover sheet decrease weed growth and/or increases weed disease development in the weed-infested turfgrass as compared to in the absence thereof.

12. The method of claim 11, wherein the effective amount is of at least 1.6 g/m² of the weed-infested turfgrass and wherein the effective amount is applied on weeds.

13. The method of claim 11, wherein most of the particles have a particle size of:
  (a) less than or about 4 mm of diameter;
  (b) less than or about 3 mm of diameter;
  (c) less than or about 2 mm of diameter;
  (d) between about 1.4 mm and about 2 mm of diameter;
  (e) less than or about 1.7 mm of diameter;
  (f) less than or about 1.6 mm of diameter;
  (g) less than or about 1.5 mm of diameter;
  (h) less than or about 1.4 mm of diameter;
  (i) between about 1 mm and about 1.4 mm of diameter; or
  (j) less than or about 1 mm.

14. The method of claim 11, wherein said *Sclerotinia* is a *Sclerotinia minor*.

15. The method of claim 14, wherein said *Sclerotinia minor* is of the IMI 344141 isolate deposited 26 Feb. 1991 in the International Mycological Institute.

16. The method of claim 11, wherein said *Sclerotinia* is formulated into barley-based particles.

17. The method of claim 11, wherein said *Sclerotinia* is formulated into:
  (a) barley-based, millet-based, rice-based or wheat-based particles;
  (b) sodium-alginate-based particles; or
  (c) kaolin clay-based particles.

18. The method of claim 11, wherein said weed is:
  (a) broadleaf weed;
  (b) dandelion;
  (c) broadleaf plantain;
  (d) narrow leaf plantain;
  (e) ground ivy;
  (f) prostrate knotweed; or
  (g) white clover.

19. The method of claim 11, further comprising a sticking agent coated on the particles.

20. The method of claim 19, wherein the sticking agent is:
  (a) Carrageen seaweed-based;
  (b) Irish Moss Powder; or
  (c) Acacia gum.

21. The method of claim 11, wherein said ground covering sheet comprises jute.

22. The method of claim 11, wherein said ground covering sheet consists of jute.

23. The method of claim 11, wherein said ground covering sheet comprises synthetic fibres.

24. The method of claim 17, wherein said *Sclerotinia* is formulated into barley-based particles.

25. The method of claim 11, wherein the effective amount is of at least 0.4 g/plant.

26. The method of claim 11, wherein the effective amount is between about 10 g/m² and about 120 g/m² of the weed-infested turfgrass.

27. The method of claim 11, wherein the effective amount is between about 10 g/m² and about 60 g/m² of the weed-infested turfgrass.

28. The method of claim 11, wherein the effective amount is between about 20 g/m² and about 120 g/m² of the weed-infested turfgrass.

29. The method of claim 11, wherein the effective amount is between about 20 g/m² and about 30 g/m² of the weed-infested turfgrass.

30. The method of claim 11, wherein the effective amount is between about 20 g/m² and about 60 g/m² of the weed-infested turfgrass.

31. The method of claim 11, wherein the effective amount is between about 30 g/m² and about 120 g/m² of the weed-infested turfgrass.

32. The method of claim 11, wherein the effective amount is between about 30 g/m² and about 60 g/m² of the weed-infested turfgrass.

33. The method of claim 11, wherein the effective amount is between about 40 g/m² and about 120 g/m² of the weed-infested turfgrass.

34. The method of claim 11, wherein the effective amount is between about 40 g/m² and about 60 g/m² of the weed-infested turfgrass.

35. The method of claim 11, wherein the effective amount is between about 60 g/m² and about 120 g/m² of the weed-infested turfgrass.

36. The method of claim 11, wherein the effective amount is about 20 g/m² of the weed-infested turfgrass.

* * * * *